United States Patent [19]

Robinson et al.

[11] Patent Number: 5,494,032

[45] Date of Patent: Feb. 27, 1996

[54] OXIMETER FOR RELIABLE CLINICAL DETERMINATION OF BLOOD OXYGEN SATURATION IN A FETUS

[75] Inventors: Mark R. Robinson; David M. Haaland, both of Albuquerque, both of N.M.; Kenneth J. Ward, Madison, Wis.

[73] Assignee: Sandia Corporation, Albuquerque, N.M.

[21] Appl. No.: 247,297

[22] Filed: May 23, 1994

Related U.S. Application Data

[63] Continuation of Ser. No. 729,452, Jul. 12, 1991, abandoned.

[51] Int. Cl.[6] ........................................ A61B 5/00
[52] U.S. Cl. .................... 128/633; 128/664; 128/666; 356/41
[58] Field of Search ................................ 128/633–634, 128/664–666; 356/41

[56] References Cited

U.S. PATENT DOCUMENTS

| H1,114 | 12/1892 | Schweitzer et al. | |
|---|---|---|---|
| 4,114,604 | 9/1978 | Shaw et al. | |
| 4,407,290 | 4/1983 | Wilber | |
| 4,653,498 | 3/1987 | New et al. | |
| 4,658,825 | 4/1987 | Hochberg et al. | |
| 4,800,885 | 1/1989 | Johnson | |
| 4,809,681 | 3/1989 | Kantrowitz et al. | |
| 4,846,183 | 7/1989 | Martin | |
| 4,859,057 | 8/1989 | Taylor et al. | |
| 4,975,581 | 12/1990 | Robinson et al. | 128/633 |
| 5,131,391 | 7/1992 | Sakai et al. | 128/633 |
| 5,203,259 | 4/1993 | Takatani et al. | 128/633 |
| 5,228,440 | 7/1993 | Chung et al. | 128/633 |
| 5,246,002 | 9/1993 | Prosser | 128/633 |
| 5,313,941 | 5/1994 | Braig et al. | 128/633 |

OTHER PUBLICATIONS

Bowes, Watson A., Barry C. Corke, Jaroslav Hulka: "Pulse Oximetry: A Review of the Theory, Acuracy, and Clinical Applications". *Obstetrics and Gynecology* Sep. 1989, vol. 74, No. 3, Part 2, p. 541.

Hoeft, A., H. Korb, J. Steinman, R. DeVivie: "In Vivo Measurement of Blood Oxygen Saturation by Analysis of Whole Blood Reflectance Spectra". *SPIE Optical Fibrs in Medicine* 1989, vol. 1067, pp. 62–68.

Johnson, N.: "Monitoring the Fetus with a Pulse Oximeter". *First International Symposium on Intrapartum Surveillance* Oct. 1990.

Gardosi, J.: "Intrapartum $O_2$ Saturation Trend and Acidosis". *First International Symposium on Intrapartum Surveillance* Oct. 1990.

(List continued on next page.)

Primary Examiner—Angela D. Sykes
Assistant Examiner—Robert L. Nasser, Jr.
Attorney, Agent, or Firm—DeWitt M. Morgan

[57] ABSTRACT

With the crude instrumentation now in use to continuously monitor the status of the fetus at delivery, the obstetrician and labor room staff not only over-recognize the possibility of fetal distress with the resultant rise in operative deliveries, but at times do not identify fetal distress which may result in preventable fetal neurological harm. The invention, which addresses these two basic problems, comprises a method and apparatus for non-invasive determination of blood oxygen saturation in the fetus. The apparatus includes a multiple frequency light source which is coupled to an optical fiber. The output of the fiber is used to illuminate blood containing tissue of the fetus. In the preferred embodiment, the reflected light is transmitted back to the apparatus where the light intensities are simultaneously detected at multiple frequencies. The resulting spectrum is then analyzed for determination of oxygen saturation. The analysis method uses multivariate calibration techniques that compensate for non-linear spectral response, model interfering spectral responses and detect outlier data with high sensitivity.

14 Claims, 23 Drawing Sheets

OTHER PUBLICATIONS

Chapman, K. R., F. L. W. Liu, R. M. Watson, A. S. Rebuck: "Range of Accuracy of Two Wavelength Oximetry", *Chest* Apr. 1986, vol. 89, No. 4, pp. 540–542.

Severinghaus, John W., Karen N. Naifeh: "Accuracy of Response of Six Pulse Oximeters to Profound Hypoxia". *Anesthesiology* Oct. 1987, vol. 67, No. 4, pp. 551–558.

Pleat, S., M. Booker, C. Lanigan, J. Ponte: "Continuous Intra partum Measurement of Fetal Oxygen Saturation". *The Lancet* Jul. 23, 1988, p. 213.

Johnson, N., R. J. Lilford: "Continuous Intrapartum Measurement of Fetal Oxygen Saturation". *The Lancet* Aug. 27, 1988, p. 517.

Johnson, N., V. A. Johnson, J. Bannister, R. J. Lilford: "Measurement of Fetal Peripheral Perfusion with a Pulse Oximeter". *The Lancet* Apr. 22, 1989, p. 898.

Gardosi, J., M. Carter, T. Becket: "Continuous Intrapartum Monitoring of Fetal Oxygen Saturation". *The Lancet* Sep. 16, 1989, pp. 692–693.

Smits, T. M., J. G. Aarnoudse: "Variability of Fetal Scalp Blood Flow during Labour: Continuous Transcutaneous Measurement by the Laser Doppler Technique". *British J of Obstetrics and Gynaecology* Jun. 1984, vol. 99, pp. 524–531.

Johnson, N., V. A. Johnson: "Continuous Fetal Monitoring with a Pulse Oximeter: A Case of Cord Compression". *Am J. Obstetrics Gynecol* Nov. 19—, pp. 1295–1296.

Johnson, N., V. A. Johnson, J. Bannister, G. Lyons, R. J. Lilford, M. Griffith–Jones, D. Tuffnell, J. L. Onwude: "Monitoring the Fetus with a Pulse Oximeter during a Caesarean Section". *British J of Obstetrics and Gynaecology* Jul. 1990, vol. 97, pp. 653–658.

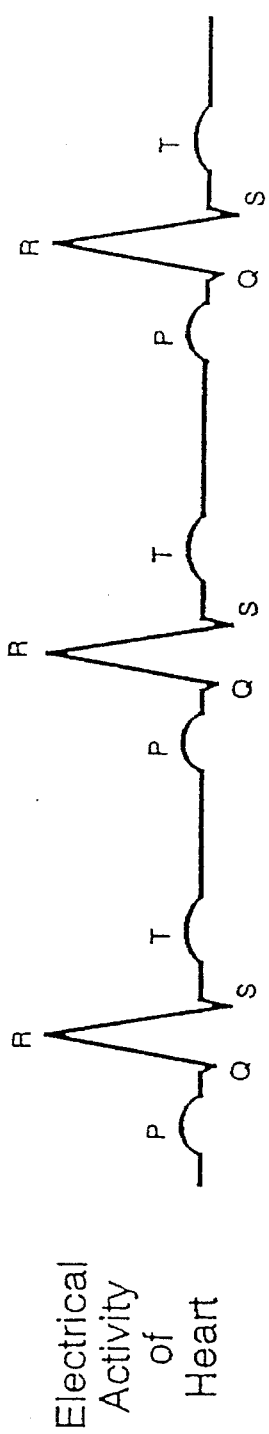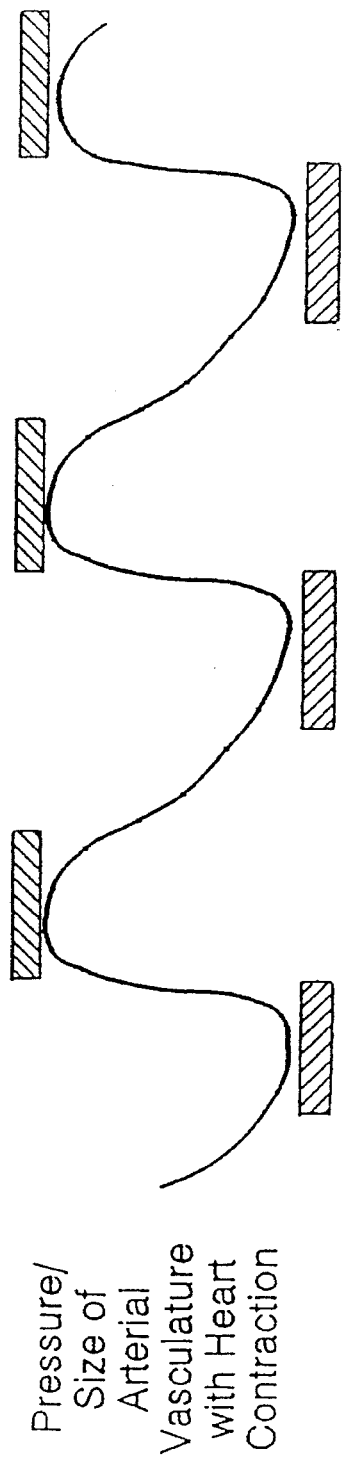
FIG-23

OXIMETER FOR RELIABLE CLINICAL DETERMINATION OF BLOOD OXYGEN SATURATION IN A FETUS

This is a continuation of application Ser. No. 07/729,452 filed on Jul. 12, 1991 abandoned.

BACKGROUND OF THE INVENTION

This invention relates to both a method and apparatus, as illustrated in FIG. 1, for the non-invasive determination of blood oxygen, particularly in a fetus.

Oxygen is essential to human life; for the adult, child and fetus. Asphyxia is the condition where the lack of oxygen causes the cessation of life. Hypoxia is a deficiency in the amount of oxygen reaching the tissues. While hypoxia is not fatal it may cause severe neurological damage.

The first manifestation of fetal hypoxia is a decrease in oxygen content and an accumulation of carbon dioxide in the blood. The latter, in turn, causes a decrease in the pH values of the blood resulting in respiratory acidosis. In the second stage there is an additional build up of organic acids due to anaerobic glycolysis. In the third stage the acidosis, which has progressed in the meantime and which is predominantly of metabolic character, begins to have a negative effect on the neurological health of the fetus. The central nervous system becomes depressed and irreversible changes can occur depending upon the duration of the hypoxic condition. This, in turn, can result in brain damage and/or cerebral palsy.

Methods currently available to the obstetrician and labor room staff for assessment of fetal status include non-invasive measures such as monitoring the contraction patterns of the expectant mother and monitoring fetal heart rate (either through the abdominal wall of the expectant mother or, after the cervix is minimally dilated, via an electrode placed in the scalp or buttocks of the fetus). In the presence of possible fetal distress suggested by clinical evaluation, or non-invasive monitoring methods, or invasive procedures such as intermittent fetal scalp blood samples (for fetal blood pH determination), or percutaneous umbilical blood sampling (PUBS), emergent caesarean section is often performed.

With both the non-invasive or invasive measures for determining fetal status identified above, information concerning the most important physiological parameter of fetal well-being, blood oxygen saturation, is not available to the physician. Changes in fetal heart rate and blood pH are secondary manifestations of a primary condition, fetal hypoxia. The measurement of a secondary manifestation such as fetal heart rate would be adequate, provided that changes in fetal heart rate were predictably correlated with blood oxygen saturation. Unfortunately, research has shown that this correlation is not present. See Monbeit et al., "Fetal Heart Rate and Transcutaneous Monitoring During Experimentally Induced Hypoxia in the Fetal Dog," *Pediatric Research* 1988, Vol. 23, No. 6, p. 548; Blocking et al., "Effects of Reduced Uterine Blood Flow on Accelerations and Decelerations in the Heart Rate of Fetal Sheep", *Am. J. Obstetrics and Gynecology* 1986, 154 pp. 329–335; and Myers et al., "Predictability of the State of Fetal Oxygenation for Quantitative Analysis of the Components of Late Decelerations", *Am J Obstetrics Gynecology* 1973, 115 p. 1083.

In addition to the foregoing, controversies about fetal heart monitoring have existed since it was first introduced into clinical practice in 1968. Recently fetal heart monitoring has come under additional criticism because researchers have found that its use does not improve survival rate or neurological health. Additionally, the enormous rise in operative deliveries (primarily Caesarean sections) for fetal distress as the result of the introduction of continuous fetal monitoring is the major objection of some authors against the general application of this technique. The false positive indication of fetal distress in cases where actually no complication emerges is the major shortcoming of fetal heart monitoring when used as the only technique of supervision. See, Paper, "Benefits and Detriments of Fetal Heart Monitoring". *Seminars in Perinatology*, 1978, 2 p. 113.

The complementary use of a biochemical parameter with fetal heart monitoring has been proposed as an adequate solution to the foregoing concerns. To some extent fetal blood analysis is a reliable method to identify intrauterine complications. However, this technique has several disadvantages. First, the cervix must be at least 3 centimeters dilated, the fetus must be a vertex (head down) presentation, and the head must be well applied to the cervix. Second, it only provides intermittent information about the biochemical status of the fetus, and in some cases has to be repeated at short intervals if fetal heart rate patterns remain or appear pathological. Third, obtaining a fetal blood sample is difficult and it is virtually impossible to tell if it is venous blood, which contains mostly deoxygenated hemoglobin (Hb) (i.e., low $O_2$ saturation) or arterial blood which contains mostly oxygenated hemoglobin ($HbO_2$) (i.e., high $O_2$ saturation). This uncertainty results in the pH of the fetal blood being the actual perimeter measured rather than oxygen saturation. A pH decrease is an accurate measurement of hypoxia, but is often manifested too late as the condition of hypoxia must exist for quite some time. Another problem is that the sample could be that of the mother, not the fetus. Finally, a traumatization of the fetal skin is inevitable and infection may occur, as one or more incisions have to be made in order to take blood samples. Thus, this procedure is complicated with problems of inaccuracies and the potential hazards of invasive procedures and, therefore, not widely utilized. See "Methodology and Clinical Value of Transcutaneous Blood Gas Measurements in the Fetus", *Intrapartum Biochemical Monitoring of the Fetus*, 1987, p. 94.

Another invasive method to assess fetal status, but only on a one time basis, is by percutaneous umbilical blood sampling (PUBS). This is done by locating the umbilical cord with ultrasound guidance and, using a long needle, piercing through the abdominal wall, through the uterine wall and into the umbilical cord to obtain arterial and/or venous blood. This procedure is dangerous, requires considerable expertise and cannot be used to continuously monitor fetal well-being during labor.

The ability to determine blood oxygen saturation in both pediatric ( including newborn) and adult populations via oximetry, particularly pulse oximetry, is well known. Oximetry in such applications (but not in fetal monitoring, as explained below) is an accepted method of oxygen determination and has been utilized in clinical medicine for approximately 10 years. Basically, the oximeter provides, either non-invasively or invasively, a continuous way of determining blood oxygen saturation to assess the need for adjusting the supply of oxygen to the patient or for assessing the effect of therapies. It is essentially used to ensure that the patient's oxygen level is adequate to prevent damage to organs such as the brain, heart, lungs, and kidneys.

There are two types of oximeters: (1) invasive oximeters; and (2) non-invasive pulse oximeters. The invasive oximeters must have the light beam and detector optics in contact with blood. Thus, the light that is emitted from the instrument interacts only with blood and is then recorded by the detector. In clinical medicine the sampling device, typically a fiber optic catheter probe, is placed in a large blood vessel in the body and measurement is made on the blood that passes by the catheter. The invasive oximeters can be problematic if the catheter is abutting the wall of the blood vessel. In this circumstance the measuring probe is partially sampling the wall of a blood vessel and no accurate determination of blood saturation is made. Non-invasive (i.e., pulse) oximeters do not require direct contact with the blood. The light emitted from a pulse oximeter interacts with skin, fat, muscle, bone and blood before it is detected. The non-invasive pulse oximeters are able to remove the interferences generated by the bone, etc. by performing a ratio of or determining the difference between data from high and low pulse pressures generated by the heart of the individual being monitored. As only arterial blood pulses, non-invasive oximeters only analyze arterial blood which is pulsating, thus the name pulse oximeter. The specific method by which a pulse oximeter removes the interferences generated by skin, etc. is explained below.

An understanding of the present status of oximetry and why it is not reliable for fetal monitoring can be obtained by analyzing the state of the art which, for convenience, can be divided into: (1) existing patented technology; (2), technology published in current literature; and (3) the published attempted use of existing technology for fetal oximetry.

The prior patented technology can be broken down into three categories:

1) Non-invasive blood oxygen saturation determination instruments utilizing a transmission sampling technique, with analysis based on two wavelengths: U.S. Pat. Nos. 4,859,056, 4,846,183, 4,824,242, 4,807630, 4,807,630, 4,807,631, 4,800,885, 4,781,195, 4,714,341, 4,603,700, 4,586,513, 3,847,483 and 3,638, 640. U.S. Pat. Nos. 4,770,179, 4,700,708, 4,653,498 and 4,621,643 to New et al. are believed to represent the best examples of this technology and are assigned to Nellcor, Inc., a leading manufacturer of pulse oximeters.

2) Invasive blood oxygen saturation determination instruments utilizing a fiber optic probe with reflectance sampling in which the probe must be inserted into a blood containing area: U.S. Pat. Nos. 4,830,488, 4,813, 421, 4,807,632, 4,697,593, 4,651,741, 4,623,248, and 4,523,279. U.S. Pat. No. 4,114,604 to Shaw et al. is believed to represent the best example of this prior art. The Abbott Critical Care Oximetrix 3 instrument is believed to be based on this patent.

3) Non-invasive blood oxygen saturation determination utilizing a reflectance method with analysis of the reflected light by a linear algorithm employing only two wavelengths. This technology is represented by U.S. Pat. No. 4,859,057 to Taylor et al.

The methods disclosed in the above-identified patents on pulse oximetry (e.g. New et al. and Taylor et al.) are based upon several related facts. First, the concentration of blood in a given location of the body varies with each pulse of the heart. With each heart beat a systolic pulse pressure is generated which leads to a maximal expansion (i.e. dilation) of the vascular system. During the resting period of the cardiac cycle (i.e., diastole) there is no pressure generated and the vascular system returns to a minimal size. This variation can be measured with optically based methods, by introducing a light source near the skin and detecting either the reflected or the transmitted light intensity. The light transmitted or reflected during diastole (i.e., the period when the arterial system is at its minimal size) interacts with the skin, fat, bone, muscle and blood. Light transmitted or reflected during systole, (i.e., the period of maximum expansion of the arterial system) interacts with the same skin, fat, bone, muscle, and blood, plus an additional amount of blood which is present due to the expansion of the arterial system. If the diastolic signal is subtracted from the systolic signal the result is a signal which represents the additional amount of blood. The subtraction process removes the interferences created by the interaction of the light with the skin, fat, bone and muscle. The quality and clarity of the subtraction generated signal is related to the amount of additional blood present which, in turn, is proportional to the pulse pressure, (i.e., the difference between systolic pressure and diastolic pressure). See FIG. 2 for a graphical representation of the above process. Note that invasive oximeters do not perform any type of pulse related subtraction because the light interacts with blood only and no removal of other interferences is necessary.

All present pulse instruments assess variations in red blood cell concentration by utilizing a light frequency near or at the isobestic point, where measurement of pulsatile volume is made independent of oxygen saturation. An isobestic wavelength is one which does not change intensity with oxygen saturation but only with blood concentration. Consequently, such a wavelength (typically in the range of 800–1000 nm) intentionally eliminates information on oxygen saturation and establishes a reference. A second wavelength in the red portion of the spectrum, which is sensitive to oxygen saturation, is detected by either a transmission or reflection sampling technique. By using the isobestic wavelength as a reference and by comparing its spectral intensity to the intensity of the second wavelength in the red portion of the spectrum, it is possible to determine the oxygen saturation of the blood non-invasively.

Oximeters based on invasive procedures also use a frequency at or near the isobestic point. In invasive instruments the intensity at the isobestic frequency is related to the amount of light returning or reflected by the sample which, in turn, is related to the hematocrit (i.e., the percent volume of the blood volume occupied by red blood cells). Basically, invasive methods simply take a ratio of the "red" wavelength divided by the isobestic wavelength.

An additional similarity among existing oximeters, both invasive and non-invasive, is the irradiation of the tissue or blood with only one wavelength at a given time. In U.S. Pat. No. 4,653,498 to New et al. and U.S. Pat. No. 4,859,057 to Taylor et al. the respective inventions utilize a red light source and an infrared light source which are energized at different instants in time. In the patents to Shaw et al., U.S. Pat. Nos. 3,847,483 and 4,114,604, light-emitting diodes corresponding to 3 separate wavelengths are energized at a set percentage of the operating cycle, in a non-overlapping relationship by a repetitive pulse generator. Thus, the instruments disclosed in all prior patents of which we are aware are limited by their inability to obtain information at a variety of wavelengths simultaneously due to the fact that a single detector element is used. Additionally, the sampling rate is limited by the time necessary for the light source at a given wavelength to obtain an appropriate brightness and stability.

In all prior known applications, the algorithm (i.e., a procedure for solving a given type of mathematical problem) used for analysis of the two, or sometimes three, wavelengths detected have typically utilized a single analysis frequency with a single background correction frequency to determine a single proportionality constant describing the relationship between absorbance and concentration (i.e., univariate or one variable algorithms). In the patents to New et al. the blood oxygen saturation determination is made by utilizing a ratio between the ambient transmission and the change in transmission occurring during each pulse at both wavelengths. The remainder of the univariate algorithm consists of a manipulation of this ratio in conjunction with several constants for saturation determination (see columns 13–15 of U.S. Pat. No. 4,653,498). The net result is that New et al. describe a multi-parameter but univariate method utilizing two wavelengths for oxygen saturation determination.

The invasive apparatus described by Shaw, et al., U.S. Pat. No. 3,847,483, uses an optical catheter for determination of oxygen saturation in a blood vessel or other blood filled container. The apparatus uses two wavelengths of light which originate from two light-emitting diodes, which are alternately energized for about 25% of the operating cycle in a non-overlapping manner. The oxygen saturation is then determined by an equation, which may be characterized as a nonlinear, bivariate algorithm, employing 6 calibration constants. A subsequent U.S. Pat. No. 4,114,604, also to Shaw, et al., discloses what is described in the Abstract as an "improved catheter oximeter [which] operates on radiation at three or more different wavelengths applied to and scattered back from blood under test to provide an indication of oxygen saturation and is considerably less sensitive to accuracy-degrading variations in the blood and its environment and in the oximeter measuring system." The actual saturation determination is made by using 2 ratios calculated from light intensity measurements at 3 wavelengths. The following nonlinear, two variable equation is used for the calculation:

$$O_2 \text{ SATURATION} = \frac{A_0 + A_1(I_1/I_2) + A_2(I_3/I_2)}{B_0 + B_1(I_1/I_2) + B_2(I_3/I_2)}$$

where $A_0$, $A_1$, $A_2$, $B_0$, $B_1$, and $B_2$, are experimentally derived constants, and $I_0$, $I_1$, and $I_2$ correspond to measured intensities at 3 different wavelengths. Shaw et al. state that: "Since the relationship between oxygen saturation and the ratio of light intensities is not quite linear, the apparatus of the present invention uses piecewise linear relationships or nonlinear relationships to measure oxygen saturation, over a wide dynamic range of valves" (column 2, line 50–54). The authors further state that the "oxygen saturation measured in accordance with Equation 3 [above] is a function of the ratios of light intensity measurements which is useful for determining oxygen saturation over a narrow (emphasis added) range of valves. However, to compensate for the nonlinearities of the underlying phenomena which have significant effect over a wide dynamic range of valves, Equation 3 can be augmented by adding terms proportional to the square of a ratio of light intensities, as indicated in [Equation 4] shown below." (See column 3, lines 20–29).

$$O_2 \text{ SATURATION} = \frac{A_0 + A_1(I_1/I_2) + A_2(I_1/I_2)^2 + A_3(I_3/I_2)}{B_0 + B_1(I_1/I_2) + B_2(I_1/I_2)^2 + B_3(I_3/I_2)}$$

Thus, Shaw et al. recognize the nonlinear characteristics involved in oxygen saturation determination and recommend a possible method for overcoming this problem. It is important to note that the Shaw methodology utilizes only a few discrete non-overlapping frequencies taken at different non-overlapping time periods. It is also important to note that it is not suited to non-invasive determinations as it does not disclose any method of eliminating background components such as hair, bone and skin. This is because Shaw, et al. place their detector directly in the blood. Also, because of the extreme difficulty in inserting a catheter in the blood vessel of a newborn, let alone the essentially closed environment of a fetus, invasive procedures are not usable.

The reflectance oximeter disclosed by Taylor et al., U.S. Pat. No. 4,859,057, does not disclose as specific mathematical relationship between the two wavelengths utilized. The scope of the patent is summarized in the following: "In a further method in accordance with the invention for reflectance oximetry wherein energized and reflected light from said sources is sensed to produce red and infrared reflectance signals respectively, the method comprising separating the a.c. and d.c. components of said reflectance signals, determining the difference between the maximum and minimum valves of each pulse of said a.c. component and determining oxygen saturation from said difference by comparison of said difference with a look up table." See column 4, lines 56–66. The d.c. component corresponds to the sum or average amount of light reflected back from the tissue. The a.c. component is generated by the pulsating blood. Although the terminology is different, the net result is that Taylor, et al. subtract the minimum from the maximum components of the a.c. signal, which is the same as subtracting the systolic and diastolic signals. Again, the technology employs only two wavelengths of light, with the intensity from each wavelength being recorded at different and discrete times.

An additional methodology associated with invasive reflectance determination is disclosed by Hoeft et al., "In Vivo Measurement of Blood Oxygen Saturation by Analysis of Whole Blood Reflectance Spectra", SPIE Vol 1067 Optical Filters in Medicine IV (1989). The actual instrumentation utilized consists of an optical multichannel instrument with a grating that separates light into different wave lengths and a CCD detector array. Like other investigators, they employ a simple relationship based upon one of the two wavelength regions used being an isobestic range, (i.e., a wavelength range at which little or no difference appears in the optical reflectance of oxyhemoglobin vs. reduced hemoglobin). Oxygen saturation is then assumed to be a linear function of the ratio of the light intensity reflected from the blood at the isobestic and non-isobestic wavelengths as follows:

$$O_2 \text{ Saturation} = A + B(I_1/I_2)$$

where $I_1$ is light intensity diffusely scattered back from the blood at the isobestic wavelength, $I_2$ is the light intensity diffusely back scattered at the non-isobestic wavelength, and A and B are experimentally determined calibration coefficients. The method of Hoeft et al., differs from the other above identified methodologies in that they allow for simultaneous sampling of multiple frequencies and by summing the total light intensity from 600 to 840 nm and equating it to $I_2$. $I_1$ was found by summing the isobestic wavelengths from 840–850 nm. Thus, there is no overlap between $I_1$ and $I_2$. Additionally, the coefficients A & B are determined using a 2nd order polynomial in hemoglobin concentration. Before the $O_2$ saturation of an unknown sample can be determined, the hemoglobin of the blood sample must be known for the calculation of coefficients A & B. Although Hoeft's methodology utilizes information from more than one frequency, it uses a univariate algorithm, because only one variable results from each frequency range summation (i.e., a single number). Additionally, Hoeft's method is not suited to non-invasive analysis since it requires a determination of hemoglobin concentration via wet chemistry, for subsequent determination of coefficients A and B.

Over the past few years significant research has been done in the attempt to create a clinically useful pulse oximeter for fetal monitoring, but none have been reliable or accurate enough to reach clinical (i.e., standard/non-experimental) medicine. The reason for this failure is multi-factorial, including the difficulty of the environment and the parameters under which a fetal pulse oximeter must operate. This work has focused on modifying existing pulse oximeters for reflectance measurement.

The work by Johnson "Monitoring the Fetus with a Pulse Oximeter", *First International Symposium on Intrapartum Surveillance*, October 1990, and Gardosi "Intrapartum $O_2$ Saturation Trend and Acidosis", October 1990, *First International Symposium on Intrapartum Surveillance* have shown that the normal fetus at time of delivery has a blood oxygen saturation of approximately 60% or 75%, depending upon which investigators' results are accurate. A possible reason for this discrepancy is, as discussed below, that existing pulse (non-invasive) oximeters are inaccurate at low oxygen saturations. The work of Chapman et al., "Range of Accuracy of Two Wavelength Oximetry" *Chest*, Vol. 89, No. 4 April, 1986, pp. 540–542, and Severinghaus et al., "Accuracy of Response of Six Pulse Oximeters to Profound Hypoxia", *Anesthesiology*, Vol. 67, No. 4, Oct. 1987, pp. 551–558, have demonstrated that existing pulse oximeters are not accurate at $O_2$ saturations below 75%. Thus, the modification of existing pulse oximeters for fetal monitoring is destined for failure, because the fetus is at a saturation of less than 75%, and existing pulse oximeters do not work well below 75%.

While the inability of existing pulse oximeters to work in the fetal oxygen saturation range may seem to be an obvious oversight, there are several reasons that have inhibited development of an accurate and reliable fetal monitor. The main reasons existing oximeter technology is not suitable for fetal monitoring are: (1) the requirement that the sampling measurement be made by reflectance spectroscopy; (2) fetal circulation has a much lower pulse pressure than that of adults; (3) the critical range for making a decision on operative intervention will be in the 30% to 60% oxygen saturation region; and (4) fetal heart rate is approximately twice that of the average adult.

A comparison between transmission sampling employed by present pulse oximeters, the type used by Chapman et al. and Severinghaus et al., versus the reflectance sampling required by the environment when monitoring the fetus, reveals that it is difficult to obtain spectral data from the fetus with signal-to-noise ratios comparable to data presently obtained by oximeters from adults or newborns. In comparison to transmission measurements, the use of reflectance spectroscopy decreases the magnitude of the return signal by approximately a factor of 10. Any decrease in the amount of signal is damaging to the prediction, because of the resultant decrease in the signal-to-noise ratio. As the signal-to-noise ratio decreases, the precision of the oxygen saturation determination decreases.

A requirement of non-invasive arterial blood oxygen saturation determination is that the background components of hair, skin and bone be removed. To remove such background components, existing non-invasive oximeters use the difference between diastole and systole signals to obtain a "blood" signal that is analyzed for saturation determination. Thus, the larger the difference between systolic and diastolic, (i.e., the larger the pulse pressure differential) the larger the blood volume analyzed, and the higher the signal-to-noise ratio. While the fetus is in utero, fetal circulation is present which results in similar right and left heart pressures; specifically systolic pressures of 75–80 mm Hg and diastolic pressures of 50–55 mm Hg. Thus, the difference between diastole and systole is significantly less, approximately 20 mm Hg, in comparison to 60 mm Hg pulse pressure in the average adult. This fact has not gone unnoticed as demonstrated by Siker's statement that, "Standard monitors need larger wave-forms than the fetal scalp may generate during labor", "Reflection Pulse Oximetry in Fetal Lambs", *First International Symposium on Intrapartum Surveillance*, October, 1990. As stated by Johnson, supra, "good readings were only obtained in 25% of cases . . . ". While applicants cannot be sure of what is meant by "readings", it is strongly suspected that Johnson is referring to the signal resulting from comparison of the systolic and diastolic signals. Thus, physiological parameters present in the fetus, such as low pulse pressure and the necessity for reflectance sampling, result in decreased signal-to-noise ratios which degrade the accuracy and precision of prediction.

The environment under which the fetal pulse oximeter is required to operate is further complicated by the low oxygen saturations it is required to determine. The work of Chapman et al. and Severinghaus et al. have demonstrated that the accuracy of oxygen saturation determination becomes quite poor at saturations of less than 75%. Although not mentioned or discussed by either Chapman et al. or Severinghaus et al., the source of this error is the nonlinear relationship between oxygen saturation and reflected or transmitted light intensity, as discussed below. If one uses the oxygen saturation errors reported by Chapman et al. and Severinghaus et al. for extrapolation to fetal monitoring, their reported errors should be considered as a best case situation due to the fact that their data were obtained from adults by transmission sampling (in contrast to reflectance sampling required for a fetal pulse oximeter). Their reported fetal oximetry errors are in excess of 10% absolute error. See data from Johnson and Dassel et al. Thus, using the reported data acquired by existing technology, the oxygen saturation of the fetus cannot be determined with an error of less than 10% for the expected fetal oxygen saturations below 75%. Based upon the work of Gardosi the fetus starts to develop metabolic acidosis secondary to decreased oxygen supply at an oxygen saturation of approximately 60%. Thus, if the present technology were used in a clinical situation for monitoring a fetus during labor, an oximeter reading of 60% oxygen saturation might actually be 70%, in which case no operative intervention should be initiated. Alternatively, the saturation might actually be 50% in which case some type of operative intervention may be considered. The clinical usefulness of current oximeters for fetal applications, with a best case average error of determination of approximately 10% oxygen saturation, is questionable.

An additional problem associated with the existing technology is that the two or more wavelengths of light used for the determination of the oxygen saturation are not sampled at the same time. The process of switching between wavelengths can be done rapidly but there is a finite amount of time required for obtaining the required intensities at each wavelength. The time necessary for each data value is determined by the time required for the light emitting diode (LED) to reach a stable intensity and for the detector to record the received intensity value. Both time constraints are strongly influenced by the capacitance of the oximeter system. The lack of simultaneous frequency sampling is of less consequence in the adult population in which the normal heart rate is approximately 80 beats per minute, and beatto-beat variation in pulse pressure, caused by respiration, is quite small. In the fetus the average heart rate is between 120 and 160 beats per minute, and large variations in beat-to-beat pulse pressure are present due to uterine contractions. Because existing technology is unable to simultaneously record multiple frequencies, the same blood volume is not sampled. In the adult a given frequency could be measured at a given pulse with a second measurement occurring at the next pulse. If a similar methodology is used on the fetus, the spectral intensity values corresponding to the additional blood present are likely to correspond to different amounts of additional blood due to the variation in pulse pressure. These resulting intensity values could be used to generate a spectrum, but the spectrum would lead to imprecise analyses since the variation of the amount of blood present in sequential pulses would cause corresponding variations in the intensities at each frequency.

In summary, the physiological and physical parameters associated with fetal monitoring represent an extreme environment under which existing oximeter technology cannot operate with reasonable, clinically acceptable accuracy. While the articles presented at the First International Symposium on Intrapartum Surveillance are not prior to applicants' invention, they are cited to illustrate the continued shortcomings of existing fetal monitoring.

It is essential to realize that all prior art oximeters, both pulse and invasive, have used 3 or less measured intensities and/or two or less variables for analysis. Both New et al. and Shaw et al. use a limited number of wavelengths, but use nonlinear univariate or bivariate algorithms. No algorithm is specified in Taylor. Methods that simultaneously use two or more variables are known as multivariate methods. As used in this application, multivariate will refer to simultaneous analysis of three or more variables. Not only do multivariate statistical methods provide enhanced analysis of component concentrations, but such multivariate methods have also recently made possible the estimation of physical and chemical properties of materials from their spectra. Such multivariate statistical methods have been used in the analysis of salt water, peas, glucose and thin film dielectrics.

A simple illustration of the increased capability of multivariate methods in component concentration determination is provided by FIGS. 3A., 3B. and 3C. In FIG. 3A. one can see that an impurity component, whose spectrum overlaps that of the analyte, can affect the spectrum of the analytic band and, therefore, the accuracy of the analysis will suffer when the analysis is performed at a single wavelength $v_1$ or when ratioing $v_1$ to a reference wavelength. The measured absorbance, $A_m$, at the analysis wavelength, $v_1$, for a sample containing the impurity is different than the true absorbance, $A_t$, of the analyte at that wavelength. If the calibration curve in FIG. 3.B. is from spectra of samples containing no impurity, then the presence of the impurity in the sample will yield an apparent concentration that may be quite different from the true concentration. This error will remain undetected if the intensity was measured at only one wavelength. If the impurity is included in the calibration samples but varies randomly in concentration in the samples, a calibration plot similar to that in FIG. 3.B. will exhibit large scatter among the data, and the result will be both a poor calibration curve and concentration estimates that have poor precision for the unknown samples. However, with analysis at more than one wavelength, not only can the presence of the impurity be detected, FIG. 3.C., but if its presence is included in the calibration, quantitative analysis of the analyte is possible with multivariate calibration methods, even if the impurity and its concentration are unknown.

An indication that the unknown is different from the set of calibration samples not containing the impurity is obtained by plotting the absorbance of the calibration samples and the unknown sample spectra at two frequencies selected for analysis. As exhibited in FIG. 3.C., the spectrum of the sample containing the impurity (indicated by "x") is obviously different than that of the calibration spectra (i.e. it is an outlier). Outliers are those samples or spectra among either the calibration or unknown data which do not exhibit the characteristic relationship between composition and spectra of the other calibration samples. The sensitivity in detecting outliers is increased by increasing the number of frequencies included in the analysis. The number of independently varying impurities that can be accounted for in the analysis is also increased by increasing the number of frequencies utilized.

Accurate univariate methods are dependent upon the ability to identify a unique, isolated band for each analyte. Multivariate methods can be used even when there is overlap of spectral information from various components over all measured spectral regions. Unlike univariate methods, multivariate techniques can achieve increased precision from redundant information in the spectra, can account for base-line variations, can more fully model nonlinearities, and can provide outlier detection.

The general approach that is used when statistical multivariate methods are applied to quantitative spectroscopy problems requires calibration in which a mathematical model of the spectra is generated. See FIG. 4. This calibration model can then be used for prediction of concentrations in unknown samples. The spectra of a series of calibration standards are first obtained, such that the spectra span the range of variation of all factors which can influence the spectra of future unknown samples. Assuming that the calibration uses samples that contain all the components expected in the unknown samples and spans their expected range of variation, the calibration will be able to empirically account for (or at least approximate) non-ideal behavior in Beer's law, independent of the source of the non-ideal behavior. Nonlinearities may arise from spectroscopic instrumentation, dispersion, or intermolecular interactions. As used in this application "nonlinear" refers to any deviation in Beer's law or the inverse Beer's law relationship (i.e., which cannot be modeled with the standard linear expression $y=mx+b$; where y represents the dependent variable, x is the independent variable, and m and b are, respectively, the slope and intercept). As was noted by Shaw et al., the spectral response with changing oxygen saturation is not linear.

Once the empirical calibration relating spectra and component concentrations has been performed, then the spectrum of the unknown sample can be analyzed by a multivariate prediction step to estimate the component concentration or properties. If the calibration samples are truly representative of the unknown sample, then the result of the analysis will be an estimate which will have a precision similar to that found in the set of calibration samples. In addition, spectral residuals (i.e., the difference between measured and estimated spectra) can be used to determine if the unknown sample is similar to the calibration samples. If the unknown sample is not representative of the calibration samples (i.e., is an outlier) spectroscopic interpretation of the residuals can often be made to determine the source of any differences between unknown and calibration samples. See Haaland, David M.: "Multivariate Calibration Methods Applied to Quantitative FT-IR Analysis" in Practical Fourier Transform Infrared Spectroscopy, Industrial and Laboratory Chemical Analysis, Edited by J. R. Ferraro and K. Krishman, *Academic Press, Inc.* 1990.

The multivariate methods which are best suited for analysis of oximeter data are those that model the spectra using an inverse Beer's law model, such as principal component regression (PCR) or partial least squares (PLS). In an inverse Beer's law model the concentration of each component in the mixture is represented as a linear function of the sampled absorbance spectrum. An advantage of this multivariate approach is that the nonlinearities in the spectral response to changes in composition can be accommodated without the need for an explicit model. For the chemical components to be predicted, PCR or PLS analysis is used to construct a linearly independent set of factors based upon a set of calibration spectra (i.e., spectra for which the composition to be predicted is known). The number of these component factors which are useful for prediction (the "rank" of the model) is selected by a cross-validation procedure, which is also used to estimate the precision of subsequent predictions. PLS and PCR methods are capable of achieving accurate and precise results in the presence of linear and nonlinear dependencies in the absorbance spectrum at various frequencies. Thus, an entire spectral region can be used in multivariate analysis without the need for the spectroscopist to choose an optimal set of wavelengths for the analysis. Similarly, these methods of computation are not sensitive to linear dependencies introduced by over sampling of information at many frequencies in the construction of the calibration samples. See Cahn, et al., "Multivariate Calibration of Infrared Spectra for Quantitative Analysis Using Designed Experiments". *Applied Spectroscopy* 1988 Vol. 42 No. 5 p. 865.

U.S. Pat. No. 4,975,581 to Robinson et al. discloses a method and apparatus for, particularly, quantitatively determining the amount of glucose in a human. The method relates to determining one or more unknown concentration values of a known characteristic (e.g. glucose) via the steps of:

a. Irradiating a biological fluid (i.e., blood) having unknown values of a known characteristic (i.e., glucose) with infrared energy having a least several wavelengths so that there is differential absorption of at least some of the wavelengths by the biological fluid as a function of both the wavelengths and the known characteristic. The differential absorption causes intensity variations of the wavelengths incident from the biological fluid, as a function of the wavelengths and the unknown values.
  b. Measuring the intensity variations from the biological fluid.
  c. Calculating the unknown values of the known characteristic (i.e., glucose) in the biological fluid from the measured intensity variations utilizing a multivariate algorithm and a mathematical calibration model. The algorithm includes all independent sources of intensity variations v. wavelengths information obtained from irradiating a set of samples in which the values of the known characteristic are known. The algorithm also includes more wavelengths than samples in the set of samples. The model is constructed from the set of samples and is a function of the known values of the characteristic and the intensity variations vs. wavelengths information obtained from irradiating the set of samples.

The method can be used in vivo and non-invasively, in vivo and invasively, and in vitro.

The apparatus disclosed in U.S. Pat. No. 4,975,581 includes:

a. A source of infrared energy having at least several wavelengths.
  b. Apparatus for coupling the source of the infrared energy to the biological fluid to enable the biological fluid to differentially absorb at least some of the wavelengths. The differential absorption causes intensity variations of the infrared energy incident from the biological fluid as a function of the several wavelengths and of the unknown value of the known characteristics.
  c. Apparatus for measuring the intensity variations.
  d. A computer including:
    i. A stored model constructed from a set of samples in which the values of the known characteristic are known. The model is a function of the known values from the set of samples and intensity v. wavelength information obtained from the set of samples.
    ii. An algorithm including (a) all independent sources of intensity variations v. wavelengths information from both the set of samples and the biological fluid and (b) more wavelengths than samples. The algorithm utilizes the model for calculating the unknown value of the known characteristic of the biological fluid from the measured intensity variations from the biological fluid.

The applicants recognize that the preferred embodiment of U.S. Pat. No. 4,975,581 utilizes the partial least squares algorithm. However, the reasons for utilizing the PLS algorithm in the present invention are quite different from the reasons it was utilized to determine glucose concentrations. The limiting factor in the determination of a blood analyte, such as glucose, is the lack of information available. For example, when a diabetic develops a high or low blood sugar condition they do not turn another color. This lack of visible change is in stark contrast to the profound visual changes observed when someone becomes hypoxic. The person turns blue. The determination of a blood analyte requires a very high signal-to-noise ratio and a sophisticated algorithm for extraction of a minuscule amount of information (glucose is, normally, 0.1 weight percent of blood). In the case of a pulse oximeter suitable for fetal monitoring, the information is abundant (i.e., babies that are profoundly hypoxic are blue), but the environment of operation is extreme. As has been previously mentioned and will later be emphasized, the reflected light-oxygen saturation relationship is highly non-linear, the signal for analysis is extremely noisy and the present invention must remove the interfering background components by correlating with the pulsating blood. Also the frequency regions used for analysis are separate (primarily visible as opposed to primarily infrared and near infrared) and the basic instrumentation is different (i.e., a Fourier transform infrared spectrometer is used for glucose determination, versus a dispersive spectrometer used in the present invention).

Despite past and continuing failures, an accurate assessment of fetal oxygen saturation can be obtained by measuring the peripheral blood oxygen saturation in the fetus. The technology for the realization of this goal, no more invasive than the electronic heart monitors currently used, is disclosed herein. This improved method and apparatus should lead to a reduction in the rate of Cesarean sections for apparent fetal distress and the total elimination of the invasive technique of fetal blood sampling. In this way a fetus born in the best possible condition will result, while operative intervention is kept to the necessary minimum. Further, such a monitor could serve to improve the survival rate of otherwise compromised fetuses by early and accurate detection of real problems. Thus, the ultimate goal of a healthy mother and baby will be enhanced.

It is an object of the present invention to provide a fetal oximeter which can easily and accurately operate in the extreme environment of fetal monitoring, thus overcoming the shortcomings of existing technology.

The object of the pulse oximeter of the present invention is to overcome the limitations of prior art oximeters, including their inability to obtain information at a variety of wavelengths simultaneously, and the limitation inherent in the time necessary for the intermittently energized light sources in such prior art oximeters to reach the required brightness and stability.

In contrast to Shaw et al., another object of the present invention is to utilize multiple frequencies with simultaneous sampling, employ an algorithm which can model nonlinearities over the entire clinically observed blood oxygen saturation range and which is suitable for non-invasive measurements in the fetus' environment.

It is another and important object to determine if a sample's spectrum and subsequently determined oxygen value (from either the calibration set or the fetus) is representative of the calibration samples. This is crucial for the implementation of an accurate and reliable clinical instrument. Identifying and removing outlier samples from the calibration set will drastically improve the accuracy and precision of the analysis. Identification of outliers among the unknown samples provides information for evaluating the validity of the fetal blood oxygen saturation determination. This ability is especially important in this medical application because the consequences of hypoxia on the fetus can result in death or lifelong disability. For example, use of technology not applying outlier detection methods to a spurious spectral sample would generate an oxygen saturation value, but the resulting value could not be trusted to be accurate. Generation of a spurious spectrum could result from instrument malfunction, improper attachment of the monitor to the fetus or the chorioamniotic membrane of the mother, or some unusual physiological variation in the fetus such as sickle cell disease. If such an unreliable result was used to make a clinical decision, the fetus could suffer. According to the present invention, utilization of a pulse oximeter employing outlier detection methods would result in the generation of a "flag" when analyzing a spurious sample, indicating that the analysis was unreliable. No clinical decision would be based upon possible false information and the mother and fetus would not suffer harm.

It is another object of the invention to provide an oximeter based on a multivariate inverse Beer's law model, such as PLS or PCR, to provide the following benefits:

a. Accommodation of nonlinear spectral responses without an explicit mathematical model for the response and without a degradation in prediction accuracy;

b. Compensation for the presence of interferences of undetermined origin (e.g., chemical contaminants or physiological variations); and c. Identification of spurious or outlier samples in both the calibration samples and in the unknown samples.

No simple or obvious combination of the prior art will result in an instrument capable of non-invasively and accurately monitoring fetal oxygen saturation over wide ranges of saturation values. For instance, existing oximeters do not measure multiple wavelengths simultaneously. Therefore, the full advantages of using a powerful multivariate algorithm like PLS could not be obtained due to the limited number of frequencies available when using existing instrumentation. Though Taylor, et al., discloses reflectance sampling, all known commercially available pulse oximeters use transmission sampling. Further, conventional oximeters do not use gratings or any mechanism that separates light into its constituent wavelengths.

The present invention represents a significant advancement in apparatus and methodology by:

a. Simultaneous and rapid sampling at multiple frequencies. Rapid sampling is necessary due to the rapid rate of the fetal heart and large variations in beat-to-beat pulse pressure. To distinguish the true maximum and minimum of the vascular system, a sampling rate $\geq 50$ Hz would be desirable, and is feasible using our technology.

b. Use of an emitter/detector apparatus, in connection with fiber optics, which is well-suited for attachment to the fetus for reflection sampling. Traditional transmission oximeters are not useful due to the virtual impossibility of obtaining data by transmission sampling through the fetus during delivery, which requires that the detector and source be separated physically. The reflectance apparatus of Taylor is larger and requires a constant pressure application due to two discrete light sources. Constant pressure application would be extremely difficult to implement during fetal delivery.

c. Analysis of the spectral information with a multivariate algorithm. A multivariate analysis will be superior to either univariate or bivariate analyses because the information available at multiple frequencies can be combined to yield more information with a higher precision and reliability than the information available at one or several discrete frequencies or ratios. The preferred algorithms are known as partial least squares (PLS) and principle component regression (PCR). These algorithms are particularly well-suited for this application due to: their ability to model or approximate most nonlinearities; well-developed outlier detection methods; and ability to create a mathematical model of the spectral information using a minimal number of factors. Other suitable algorithms are classic least squares (CLS), Q-matrix method, cross correlation, Kalman filtering and multiple linear regression (MLR). MLR is sometimes referred to as inverse least squares (ILS).

d. Providing the doctor with a measure of validity or an assurance of accuracy by employing outlier detection methods. The ability to identify false negatives is extremely important because the consequences of hypoxia on the fetus can result in death or life-long neurological deficits. On the other hand, the ability to eliminate false positives will reduce the incidence of unnecessary caesarean sections, a surgical intervention with risks for both fetus and mother.

SUMMARY

A method and apparatus for determining non-invasively and in vivo the blood oxygen level in a mammal, particularly a fetus. The method includes the step of simultaneously generating a plurality of different wavelengths of light in the range of 500 nm to 1,000 nm. The wavelengths of light are used to irradiate in vivo and non-invasively blood containing tissue having an unknown blood oxygen level during the diastolic portion of the cardiac cycle so that there is differential attenuation of at least some of the wavelengths by the blood containing tissue as a function of the wavelengths. The differential attenuation causes intensity variations of the wavelengths incident from the blood containing tissue as a function of the wavelengths, the tissue and the unknown blood oxygen level. The intensity variations from the blood containing tissue during the diastolic portion are simultaneously measured to obtain a diastolic set of intensity variations v. wavelengths. The wavelengths of light are also used to irradiate in vivo and non-invasively the blood containing tissue during the systolic portion of the cardiac cycle, so that there is attenuation of at least some of the wavelengths by the blood containing tissue as a function of the wavelengths. The differential attenuation causes intensity variations of the wavelengths incident from the blood containing tissue as a function of the wavelengths, the tissue and the unknown blood oxygen level. The intensity variations from the blood containing tissue during the systolic portion are also simultaneously measured to obtain a systolic set of intensity variations v. wavelengths. Finally, the method includes the step of calculating the value of the unknown blood oxygen level in the blood containing tissue from the measured intensity variations during the diastolic portion and the systolic portion of the cardiac cycle utilizing an algorithm and a calibration model. The algorithm is a multivariate algorithm using 3 or more variables and is capable of modeling at least some nonlinearities over the entire clinically observed range of blood oxygen levels. The model is constructed from a set of calibration samples in which the blood oxygen levels are known, and are a function of the known oxygen levels and the intensity variations v. wavelengths obtained from irradiating the set of calibration samples with a plurality of different wavelengths of light in the range of 500 nm to 1,000 nm.

Preferably, the method also includes the step of determining whether the intensity variations v. wavelengths from the blood containing tissue having an unknown blood oxygen level represent an outlier. The method also includes the step of determining whether any of the calibration samples from the set of samples is a spectral or a concentration outlier. Optionally, the method may further include the steps of pretreatment of the measured intensity variations, and pretreatment of the blood oxygen level. The algorithm is selected from the group including PLS, PCR, CLS, Q-matrix method, cross correlation, Kalman filtering and MLR. Preferably the algorithm used has decreased sensitivity to noise by signal averaging the effects of intensity variations v. wavelengths when there are more intensities than independent sources of spectral variation, particularly PLS and PCR. The method may also include the step of modifying the intensity variations v. wavelengths response from the blood containing tissue to account for the amount of hemoglobin present in the blood containing tissue. Finally, the method may include the step of determining the difference between the diastolic set of intensity variations v. wavelengths and the systolic set of intensity variations v. wavelengths from the blood containing tissue. The determination of the diastolic portion and the systolic portion of the cardiac cycle is done by concurrently measuring the electrical activity of the heart.

The oximeter includes apparatus for simultaneously generating a plurality of different wavelengths of light in the range of 500 nm to 1,000 nm; apparatus for simultaneously directing at least a portion all of the wavelengths of light to a section of blood continuing tissue of a mammal having an unknown oxygen level; apparatus for simultaneously collecting at least a portion of the wavelengths of light which are directed from the blood containing tissue; apparatus for simultaneously measuring the intensity of each of the wavelengths collected; apparatus for storing the measured intensity variations v. wavelengths; a calibration model generated by a multivariate algorithm using 3 or more variables and which is capable of modeling at least some nonlinearities; apparatus for storing the multivariate algorithm which utilizes the calibration model and the stored intensity variations v. wavelengths for determination of the unknown blood oxygen saturation level; a microprocessor; and apparatus for indicating the calculated blood oxygen level.

While the principal benefit of this invention is the provision of an accurate, reliable fetal pulse oximeter, those skilled in the art will appreciate that such an oximeter and method can be used with newborns, children, and adolescents as well as adults and in other environments besides the labor room. An invasive oximeter could also be based on the invention disclosed herein.

BRIEF DESCRIPTION OF DRAWINGS

FIG. 5A is an enlarged view of the fiber optic bundle of FIG. 5;

FIG. 23 is a graphical representation of the electrical activity of the heart and its temporal relationship to the pressure or size of the vascular system.

DESCRIPTION OF THE PREFERRED EMBODIMENT

Figure 1:
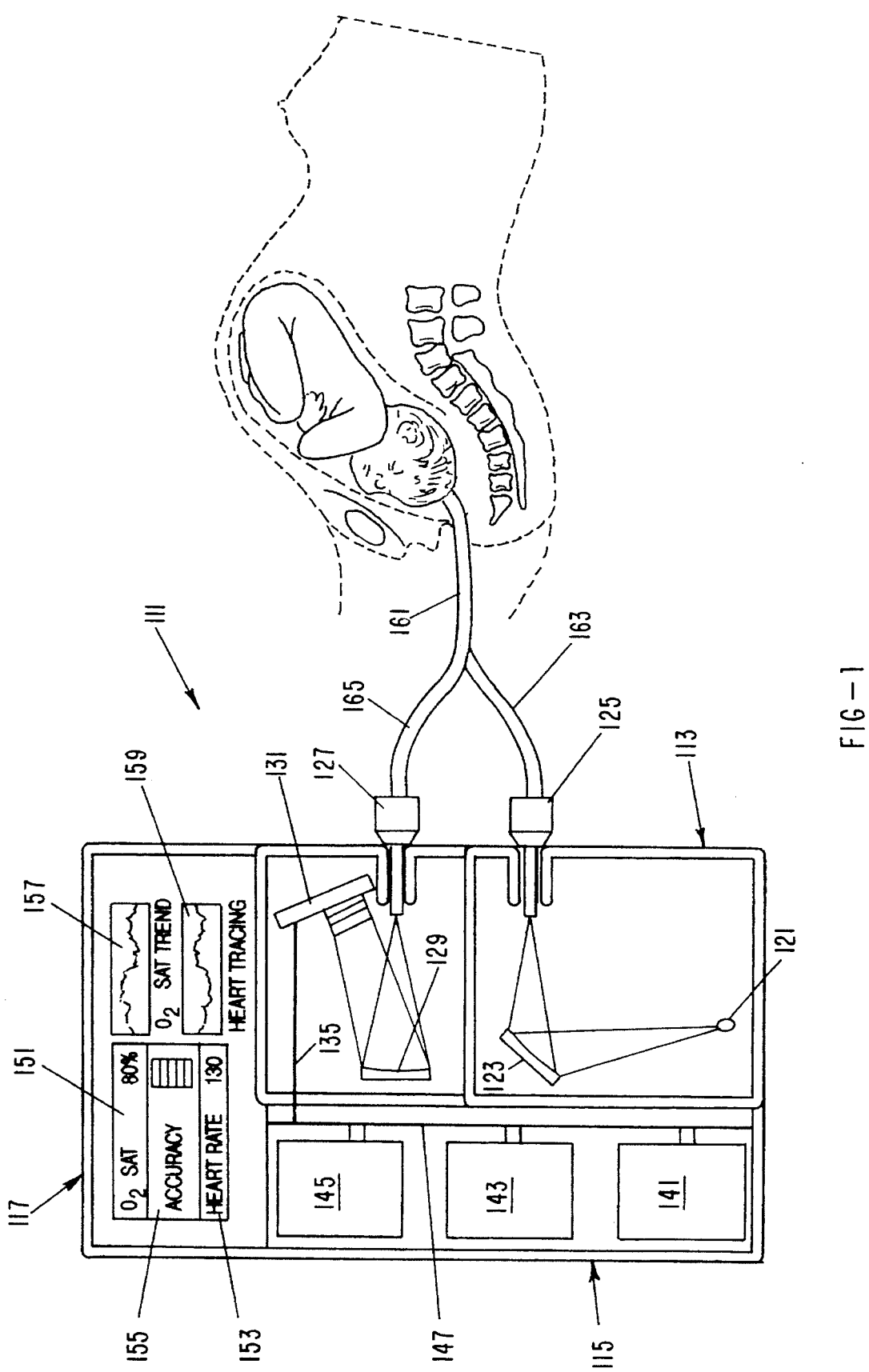
FIG. 1 is a schematic illustration of the preferred embodiment of the invention.
Figure 2:
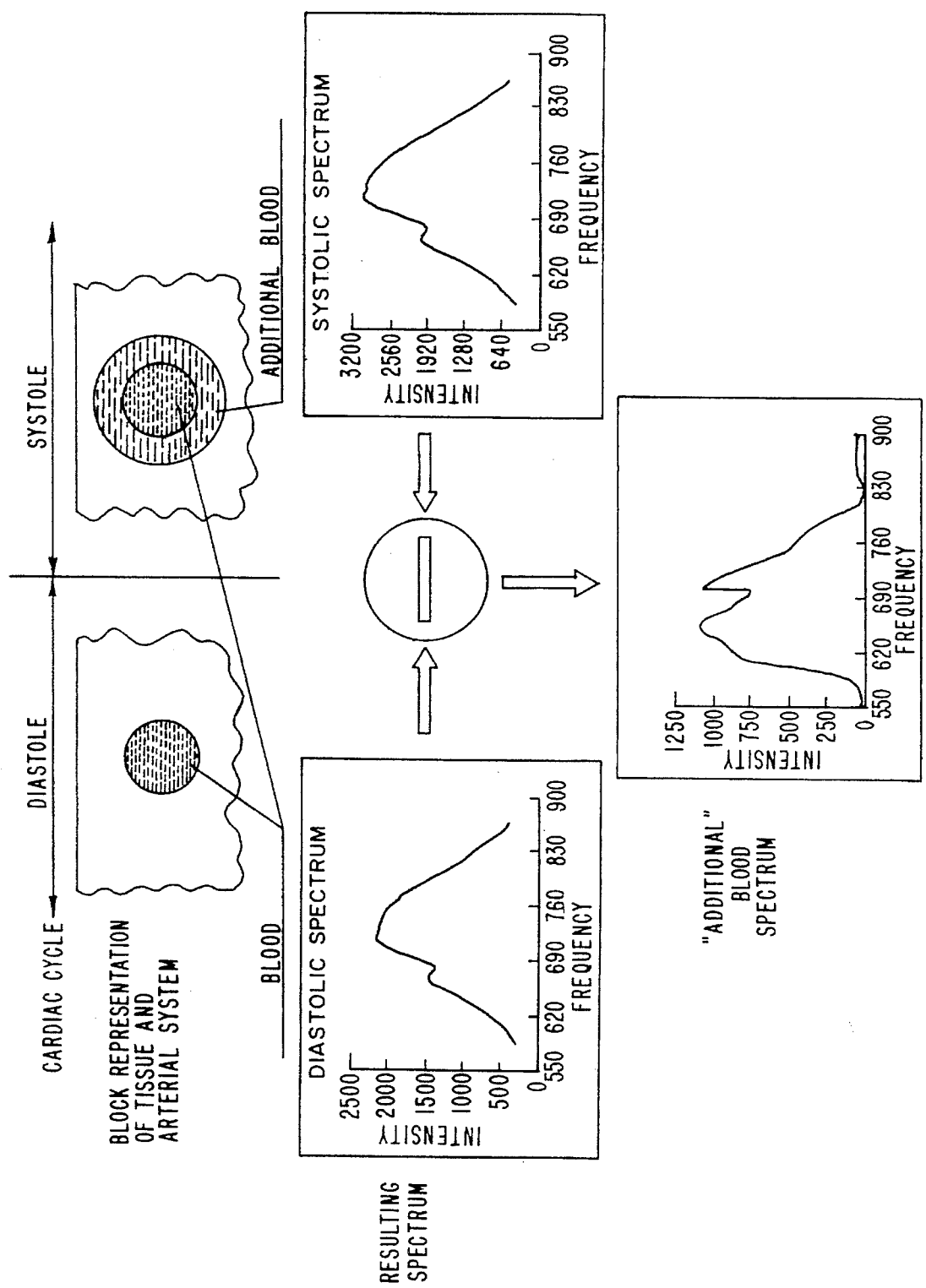
FIG. 2 is a graphical representation of the basic principle of how a conventional pulse oximeter obtains the "additional" blood signal.
Figure 3A:
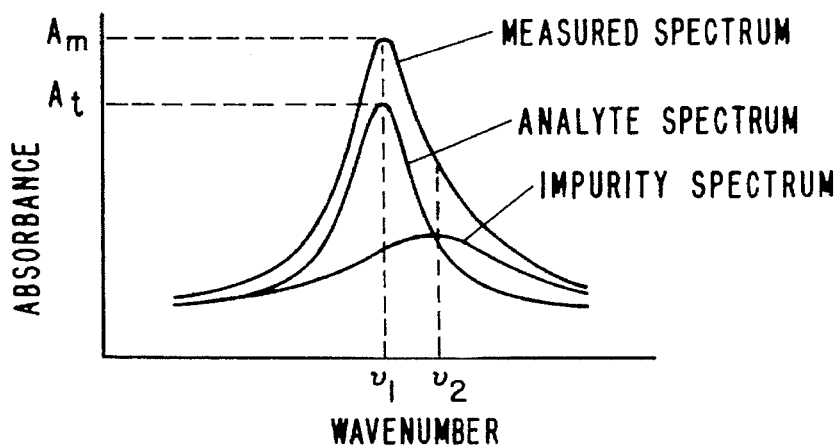
FIGS. 3B and 3C are a series of graphs comparing univariate calibration to multivariate calibration.
Figure 3B:
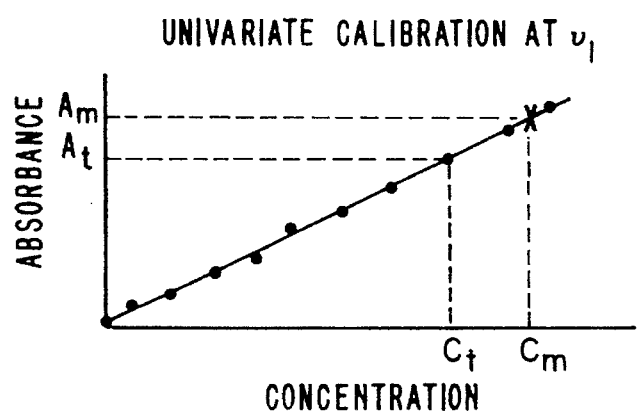
Figure 3C:
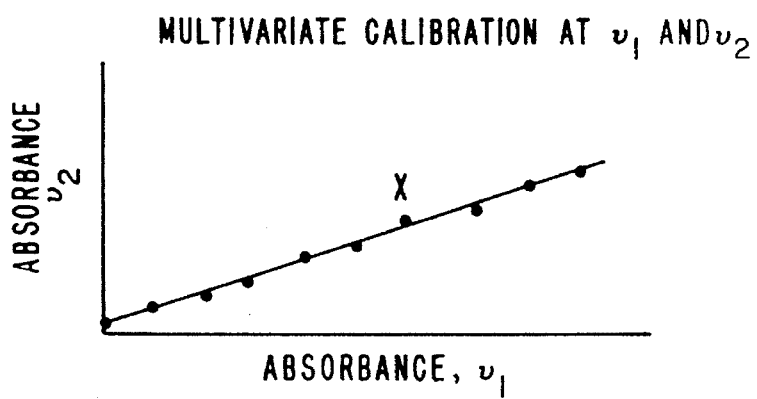
Figure 4:
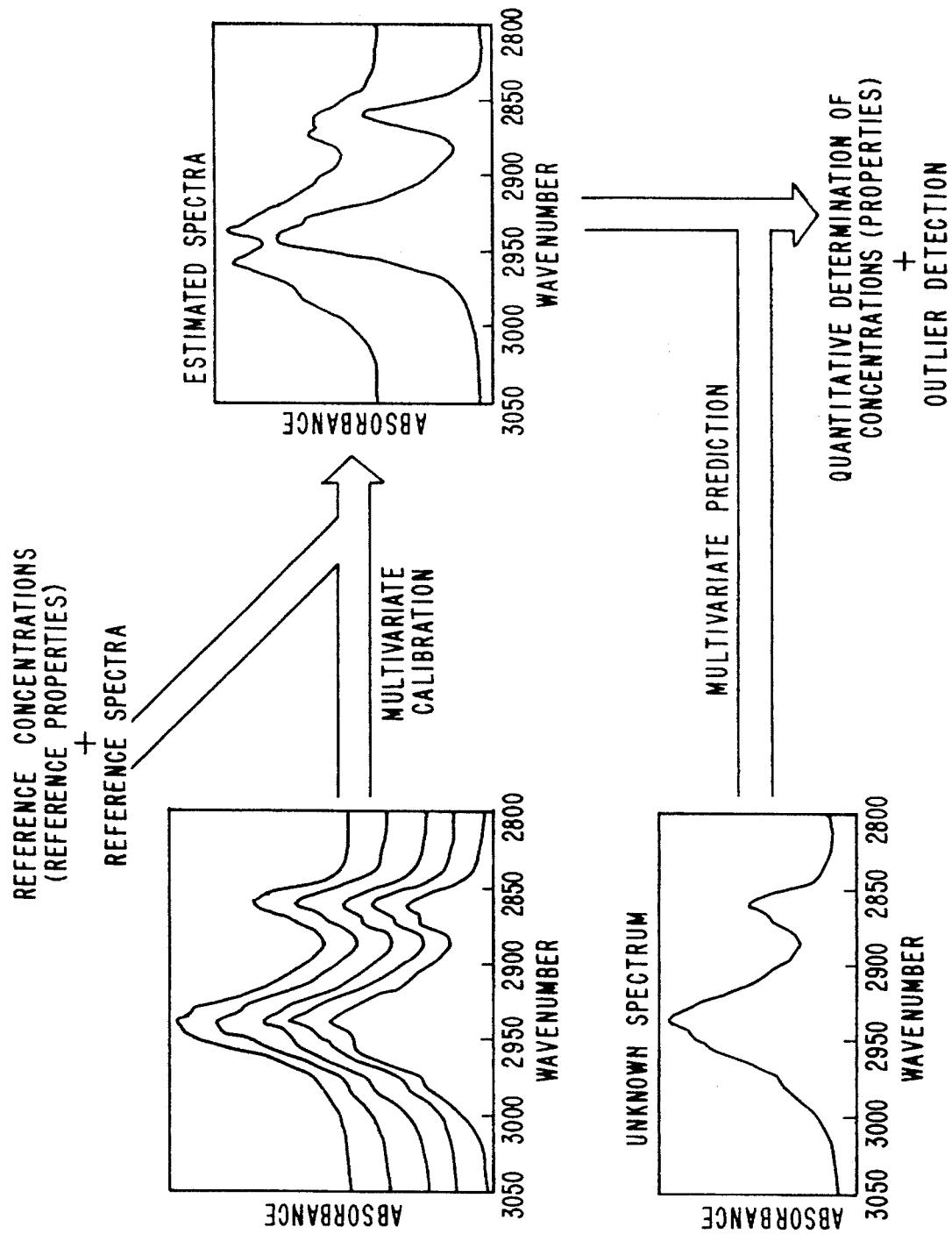
FIG. 4 is a chart showing the general approach used in multivariate statistical methods to generate a mathematical calibration model and to use this model to quantitatively determine concentrations and/or properties from the spectra of unknown samples.

To demonstrate the nonlinear reflected light response of the blood at various oxygen levels, the effect of physiological hematocrit variation, the inadequacies of the algorithms used in current oximeters, and the superiority of multivariate analysis, a set of human blood samples were examined using reflectance spectroscopy. The samples were examined at hematocrit levels ranging from 25% to 47% and with oxygen saturations ranging from 30% to 100%. Standard blood bank solutions of packed red blood cells were used to create solutions with different hematocrits. Packed red blood cells are the standard solution used for transfusion. The solutions of packed red blood cells were diluted with normal physiological saline to create hematocrit levels commonly encountered in clinical medicine. The four hematocrit levels examined were 47%, 35%, 33% and 25%. The normal physiological value for pregnant females at term is approximately 34%. See Pauerstein, Carl J., "Clinical Obstetrics" John Wiley and Sons Thus, the hematocrit of 47% is higher than normal, but is a value which is commonly seen in clinical practice. The hematocrits of 33% and 35% represent normal values while the hematocrit of 25% represents a condition of decreased red blood cell volume (i.e., anemia).

Each of the blood solutions at the above identified hematocrit levels was placed in a tonometer which allowed controlled oxygenation of blood while maintaining normal physiological temperature (i.e. 37° C./98.6° F.). The blood solutions were gently stirred to prevent settling or separation of the blood components and to provide adequate mixing. The rotational speed of the tonometer stir rod was minimized to prevent cell lysis, which was evaluated by multiple conventional extracellular potassium determinations. Potassium is concentrated inside each red blood cell to a level of 135 mmol/l, while the potassium extracellularly is quite low, at 4 mmol/l. Thus, if the cell membranes are disrupted the potassium leaks out into the extracellular fluid causing a significant rise in the extracellular potassium level. Such a significant rise was not observed, thus most of the cell membranes remained intact throughout the experiment.

The oxygenation of the blood was performed using a gaseous mixture of nitrogen, oxygen and carbon dioxide. The percentages of oxygen and nitrogen were varied to provide adequate changes in the oxygen saturation of the blood solution. The percentage of carbon dioxide was maintained throughout the experiment at a physiological level of between 4 and 8%.

Data were obtained by first establishing an appropriate hematocrit level and then varying the oxygen saturation from approximately 30% to 100%, as explained above. For each oxygen saturation examined, a 4 ml blood sample was removed from the tonometer utilizing a standard sealed syringe. A 2 ml amount of sample was placed immediately in a glass cuvette, and the syringe with the remaining 2 ml was capped. The syringe was then placed on ice to prevent changes in oxygen saturation during transport to a laboratory for conventional blood gas analysis. Placement of the sample on ice is the standard technique used in clinical practice for sample handling of arterial blood which is to undergo blood gas analysis. The oxygen saturation determination was performed at the University of New Mexico Hospital Laboratory on a Radiometer OSM3 Hemoximeter. The instrument is maintained in accordance with the manufacturer's guidelines and quality assurance is monitored using the QUALICHECK reagents S2140, S2150 and S2160 as set forth in the "OSM3 Hemoximeter Reference Manual", *Radiometer* January 1986. The records maintained for this instrument indicate that the Hemoximeter was operating with an average standard deviation of 0.3% absolute oxygen saturation for the control solutions.

Figure 5:
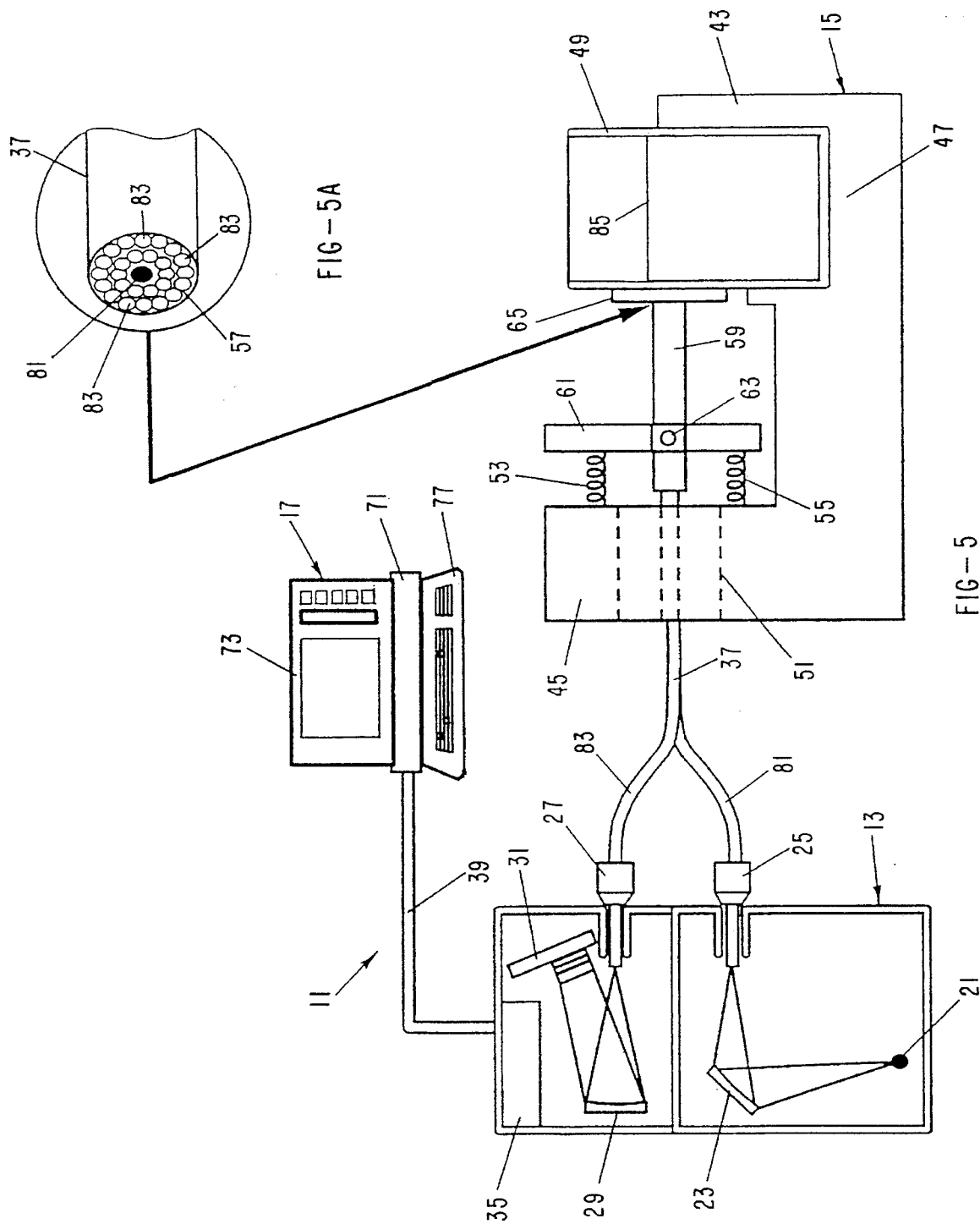
FIG. 5 is a schematic of the test apparatus of the present invention.

For each oxygen saturation examined, the 2 ml which had been placed in the glass cuvette was examined in reflectance with the test apparatus 11 illustrated in FIG. 5. Apparatus 11 includes a spectrometer 13, a cuvette holder 15 and a computer 17. Spectrometer 13 includes a halogen light source 21, a concave focusing mirror 23, a fiber optic housing 25, a second fiber optic housing 27, a grating 29, an array detector 31, and instrument electronics 35. Spectrometer 13 is connected to cuvette holder 15, via fiber optic bundle 37, and to computer 17, via cable 39. Cuvette holder 15 includes a base 41, having a first or cuvette supporting arm 43 and a second arm 45. Arm 43 includes a cavity 47 for receiving and properly positioning a standard laboratory cuvette 49. Arm 45 includes an opening 51, through which passes fiber optic bundle 37, and supports a pair of compression springs 53 and 55. The right-hand end 57 of bundle 37, which is accurately squared off, is securely contained in a rigid sleeve 59 which, in turn, is held in bracket 61 via set screw 63. Springs 53, 55 hold end 57 with reproducible contact against spacer slide 65 which, in turn, is passed into contact with one of the sides of cuvette 49. Computer 17 includes a microprocessor and associated electronics 71, video monitor 73, disk drive 75, and a key board 77. As illustrated in FIGS. 5 and 5A, bundle 37 includes a central illumination or input fiber 81 and a surrounding bundle of receiving or output fibers 83.

Again, with reference to FIG. 5, quartz-halogen light source 21, generating light in the 500 nm to 1000 nm frequency region, is coupled into fiber optic bundle 37 to provide illumination of sample 85. The central fiber 81 serves as the illumination fiber while surrounding fibers 83 serve as receivers for transporting the reflected light from the sample back to spectrometer 13. The reflected light is then separated by frequency using a standard grating spectrometer and recorded utilizing a charge coupled device (CCD) array detector 31, specifically a Phillips module type 56470 CCD detector array, at frequencies from 500 to 1000 nm. The detector was scanned 128 times for a total scan time of approximately one minute, with the intensity values from a given frequency subsequently coadded to improve the signal-to-noise ratio. The resulting intensity values at each frequency (i.e. single-beam spectral values) were then stored on a computer disk without further manipulation, to serve as the data set for subsequent analysis.

Figure 6:
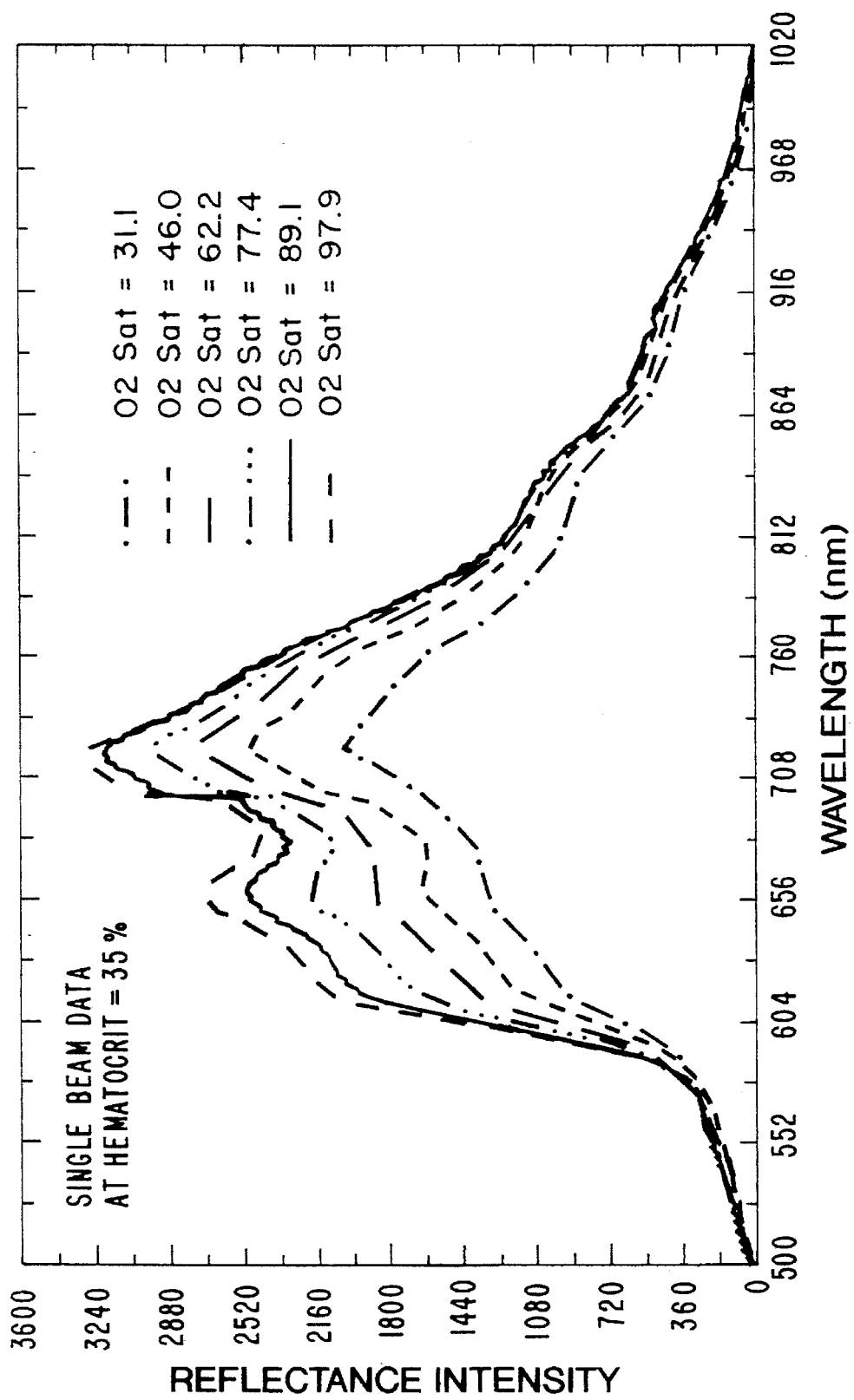
FIG. 6 is a graph illustrating the raw data (reflectance intensity vs. wavelength) obtained at various $O_2$ saturations with the apparatus of FIG. 5.

The process of establishing a hematocrit and then varying the oxygen saturation for such hematocrit was performed a number of times at each of the hematocrit levels previously identified (i.e. 47, 35, 33, 25%). Approximately 25 samples were obtained at each hematocrit level with the oxygen saturation values of these samples being distributed from 30% to approximately 100% saturation. The raw data is illustrated in FIG. 6.

The data set obtained with the apparatus of FIG. 5 was then analyzed using a variety of algorithms which represent: (1) algorithms presently utilized on commercially available oximeters and described in prior art patents; (2) algorithms published in the current literature; (3) multivariate algorithms not previously utilized for oxygen saturation determination; and (4) multivariate algorithms with isobestic correction, again not previously utilized for oxygen saturation determination. The specific algorithms and how they will be referenced are:

(1) Single ratio method as described by New et al. in U.S. Pat. No. 4,653,498;

(2) Sum of intensities ratio method, as described by Hoeft et al.;

(3) Multiple ratio method as described by Shaw et al. in U.S. Pat. No. 4,114,604;

(4) Principle component regression (PCR), not previously utilized in oxygen saturation determination;

(5) Partial least squares (PLS), not previously utilized in oxygen saturation determination; and (6) Partial least squares with isobestic correction (PLS-ic); not previously utilized in oxygen saturation determination.

Single Ratio Method

The single ratio method describes the development of a linear regression using four constants based on a ratio of intensities at 660 nm and 940 nm. Because New et al. specify the light sources as light emitting diodes (LEDs), which emit a narrow range of frequencies about their center frequency, the intensity value used for a given frequency was the average intensity value of several surrounding frequencies. To model the method and apparatus of New, et al., the 660 nm intensity value was calculated as the average of the single-beam intensities from 658 nm to 662 nm, (i.e. 5 intensity values). The value for 940 nm was obtained from 938 nm to 942 nm in a similar manner, again using 5 intensity values.

In New et al. the equation for determination of the regression constants is:

$$O_2 \text{ Saturation} = \frac{K_{B1} - RK_{B2}}{R(K_{A2} - K_{B2}) - (K_{A1} - K_{B1})}$$

Figure 7:
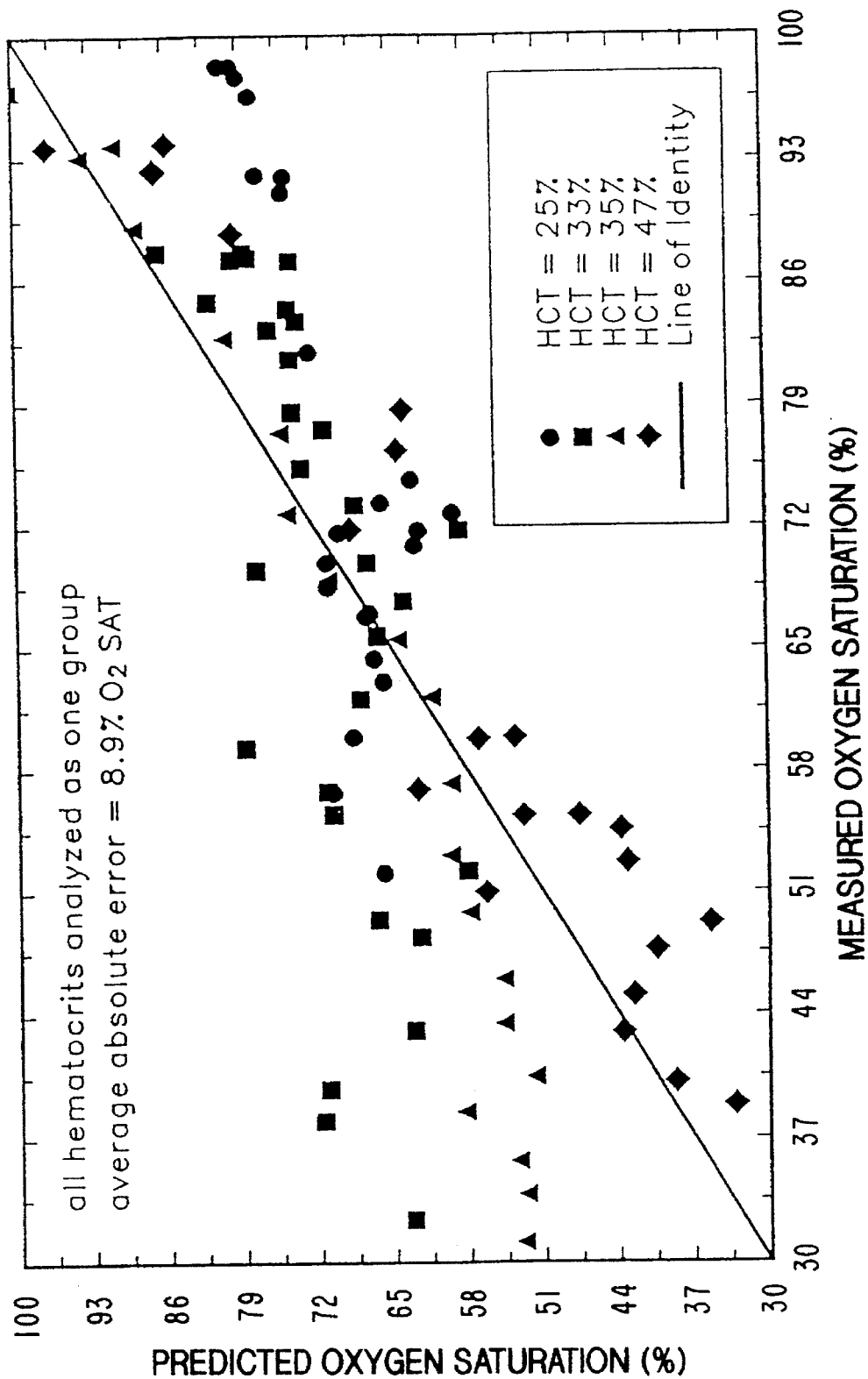
FIG. 7 is a plot of measured oxygen saturation vs. oxygen saturation predicted by analysis of a single beam spectra with the algorith of New, et al.

New, et al., specify using four different saturation values and their corresponding intensity values for determination of the regression constants (i.e., $K_{B2}$, $K_{B2}$, $K_{A1}$, $K_{A2}$). This represents a condition of four equations and four unknowns. For actual determination of the coefficient values, one of the four coefficients must be arbitrarily set, typically, to 1.0. This method of coefficient determination is feasible, but a better method to determine the constants is to utilize the intensity ratios from all calibration samples and their corresponding saturation values, and create a situation where there are many more equations than unknowns. In a condition with more equations than unknowns, a nonlinear least squares regression analysis can be performed to minimize error. We determined the constants using the modified Gauss-Newton method for the fitting of nonlinear regression functions by least squares. The analysis was performed separately at each individual hematocrit (and at all oxygen saturation levels for each hematocrit), and then upon the entire data set including all hematocrits and oxygen saturation levels together. The results are shown in FIG. 7 where Predicted Oxygen Saturation was determined by the modified Gauss-Newton method, and Measured Oxygen Saturation was determined with the Radiometer OSM3 Hemoximeter. The average errors are set forth in Table 1.

TABLE 1

| Hematocrit | Average Absolute Error of Percent Oxygen Saturation |
|---|---|
| 25% | 4.4 |
| 33% | 11.1 |
| 35% | 8.4 |
| 47% | 4.2 |
| all together | 8.9 |

Figure 8:
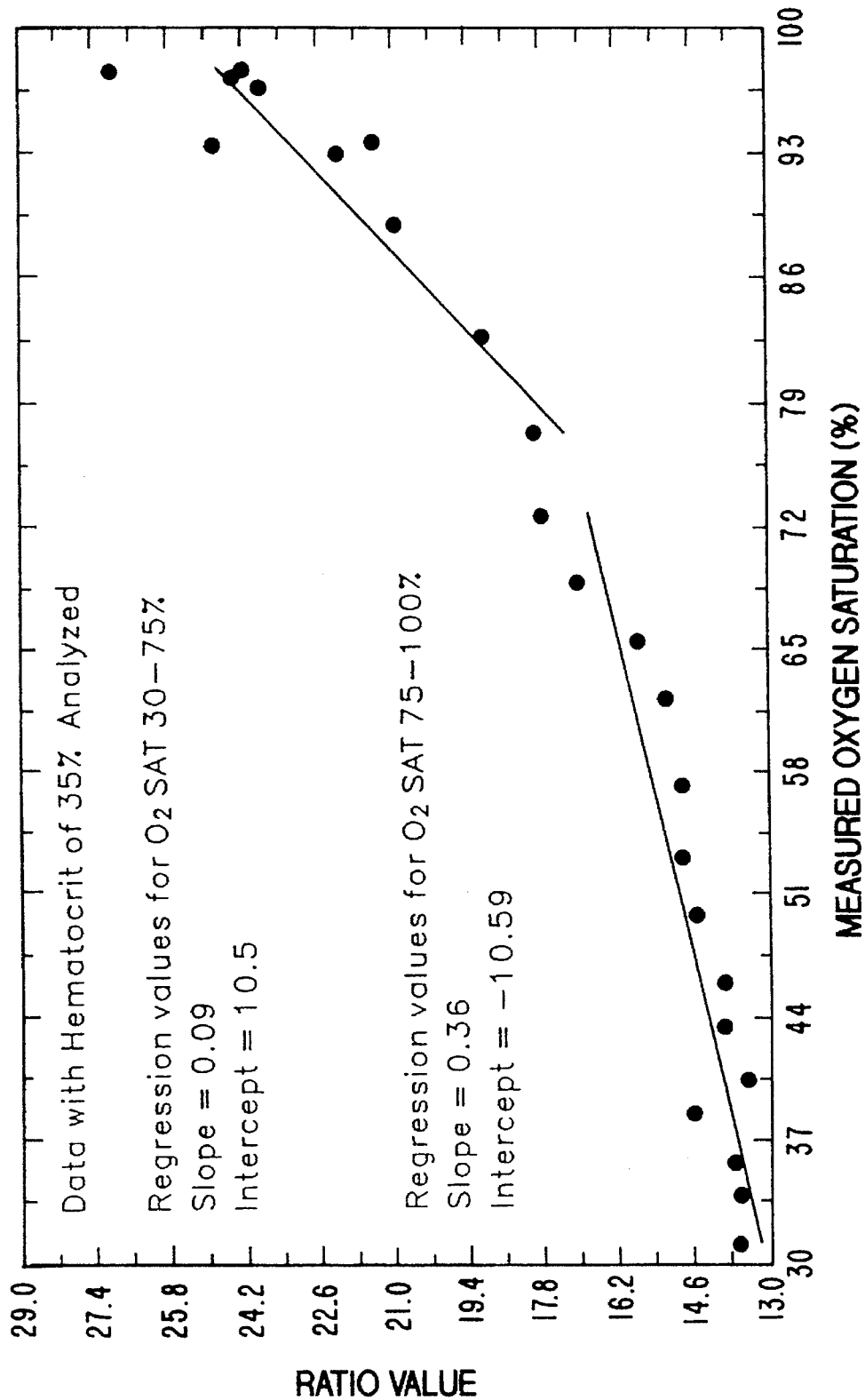
FIG. 8 is a graph illustrating the nonlinear relationship between a ratio of reflected light ratios, as specified by New, et al, and oxygen saturation, two independent regressions are shown.

To further emphasize and demonstrate the nonlinear response of the reflected light intensities versus oxygen saturation, a plot of the Ratio Value used in the New et al. algorithm versus $O_2$ Saturation at a single hematocrit (e.g., 35%) was done as shown in FIG. 8. Two least squares regressions were performed on the ratio verses $O_2$ saturation data, one for those ratios having saturations greater than 75% and a second for those ratios with saturations of less than 75%. Examination of the data, resulting regression values and corresponding regression lines, as shown in FIG. 8, reveals an inflection point at approximately 75%. It is important to understand that this nonlinear behavior causes the New et al. algorithm to preform poorly at saturations below 75%. The influence of the nonlinear behavior is exacerbated when the equation coefficients are determined at $O_2$ saturations between 75–100%, and actually results in the over estimation of $O_2$ saturation, as found by Chapman et al. and Severinghaus et al.

Intensity Sum Ratio Method

Figure 9:
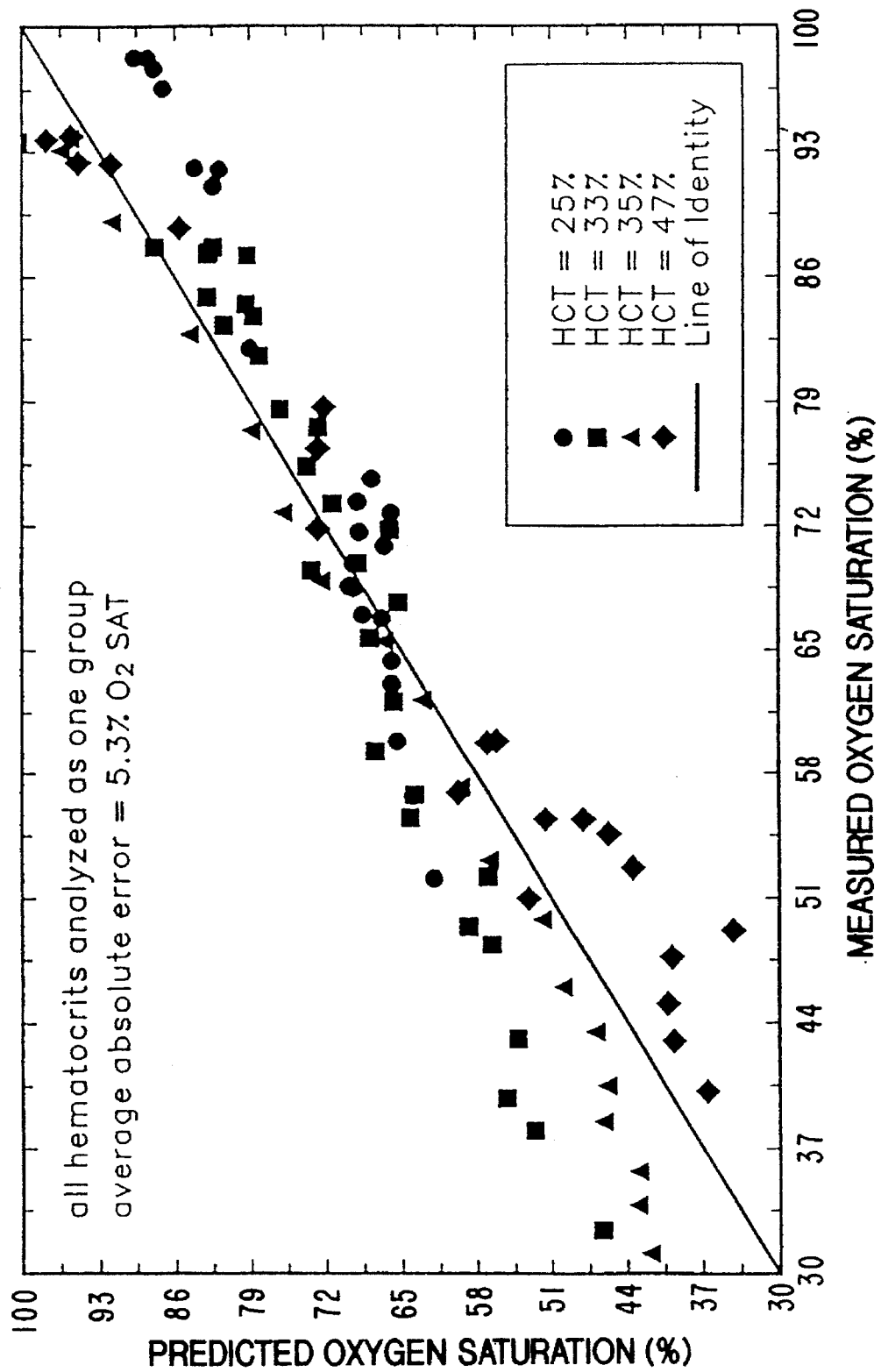
FIG. 9 is a plot of measured oxygen saturation vs. oxygen saturation predicted by analysis of the single beam spectra; and with the algorithm of Hoeft, et al.

The method as described by Hoeft et al. consists of a simple linear regression based upon a ratio of the sum of the intensities from 600 nm to 840 nm, $R_{sig}$, and a second sum of the intensities from 840 to 850 nm, $R_{ref}$. Specifically, $R_{sig}$ is the sum of 289 intensity values corresponding to frequencies between 600 nm and 840 nm, and $R_{ref}$ is the sum of 13 intensity values from 840 nm to 850 nm. The relation is stated as:

$$O_2 \text{ Saturation} = A + B(R_{ref}/R_{sig})$$

where A and B are hematocrit dependent. Utilizing the data set obtained from the apparatus of FIG. 5, a linear regression was performed on each hematocrit group individually and on the four different hematocrit groups combined together. The results are as illustrated in FIG. 9. The average errors are set forth in Table 2.

TABLE 2

| Hematocrit | Average Absolute Error of Percent Oxygen Saturation |
|---|---|
| 25% | 2.9 |
| 33% | 3.1 |
| 35% | 3.1 |
| 47% | 2.6 |
| all together | 5.3 |

Multiple Ratio Method

The U.S. Pat. No. 4,114,604 to Shaw et al. describes the use of multiple ratios utilized in a nonlinear function. The specific ratios described are $R_1$=(intensity at 669 nm)/(intensity at 698 nm) and $R_2$=(intensity at 798 nm)/(intensity at 698 nm). Again the specific intensity values used in our analysis were the average of 5 data values surrounding the specific frequency desired. Shaw et al. propose a rational function model of the form $$S = \frac{A_0 + A_1R_1 + A_2R_1^2 + A_3R_2}{B_0 + B_1R_1 + B_2R_1^2 + B_3R_2}$$

Where S is the percent oxygen saturation, the Ai's and Bi's (8 total) are model parameters, all of which have to be estimated. There is an indication that Shaw et al. realize this is excessive as they recommend certain constraints among the parameter estimates, such as $A_3=A_0+A_1+A_2$ and $B_3=B_0+B_1+B_2$, might be applied. Shaw et al. also suggest that the parameter estimates should be selected such that the partial derivative of the above equation with respect to $R_1$ should be zero near one extreme of S, while the partial derivative of S with respect to $R_2$ should be zero near the other extreme of S. If all four of these constraints are used, then there are essentially four parameters remaining in the model. However, Shaw et al. do not provide other details on how to estimate the model parameters. In trying to construct a model according to Shaw's recommendations, the constraints on $A_3$ and $B_3$ were easily incorporated into the original model. It was also necessary to set the value $B_0$ at 1 to obtain a model in which $$S_i = \frac{A_0 + A_1R_1 + A_2R_1^2 + (1 - A_0 - A_1 - A_2)R_2}{1 + B_1R_1 + B_2R_1^2 + (1 - B_0 - B_1 - B_2)R_2}$$

where $S_i$ is the model prediction associated with the $i^{th}$ observation, and $R_{1i}$ and $R_{2i}$ are the observed values of the spectral ratios ($R_1$ and $R_2$) associated with the $i^{th}$ observation.

The parameter estimates (with associated standard errors in parentheses) associated with the data set (involving data from all hematocrits) over the saturation from 30% to, approximately, 100% are $A_0$=46.6 (38);
$A_1$=−105 (89);
$A_2$=64.5 (53);
$B_1$=−2.13 (0.10); and
$B_2$=1.19 (0.11).

Figure 10:
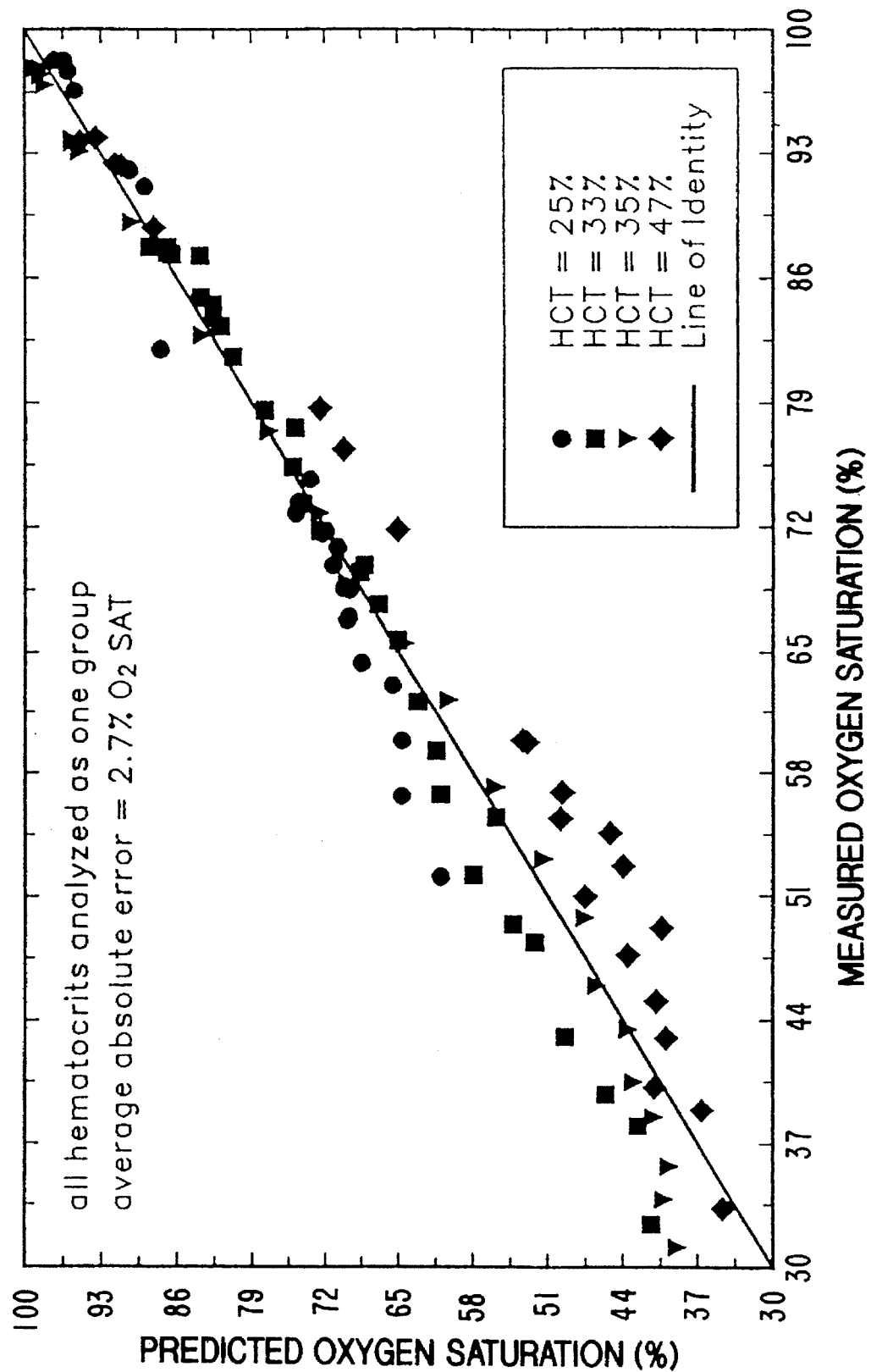
FIG. 10 is a plot of measured oxygen saturation vs. oxygen saturation predicted by analysis of the single beam spectra with the algorithm of Shaw, et al.

Estimation of the model parameters was made by nonlinear least-squares regression using the Gauss-Newton method. These parameter estimates are very highly correlated. This probably indicates that the model contains more fitted parameters than necessary, with a potential hazard that errors in the calibration data will be excessively incorporated into the model. The analysis for each hematocrit individually and for all the hematocrits grouped together is illustrated in FIG. 10. The average errors are set forth in Table 3.

TABLE 3

| Hematocrit | Average Absolute Error of Percent Oxygen Saturation |
|---|---|
| 25% | 1.4 |
| 33% | 1.2 |
| 35% | 1.2 |
| 47% | 0.9 |
| all together | 2.7 |

Multivariate Analysis

There are four full-spectrum multivariate algorithms (PLS, PCR, CLS and MLR/ILS) commonly used in spectroscopy. We have determined that the two methods best suited for accurate determination of oxygen saturation in a fetus are PLS and PCR.

To explain the superiority of full-spectrum multivariate algorithms one needs to understand that: (1) information on oxygen saturation is present at multiple frequencies, (2) full-spectrum multivariate methods have a signal averaging effect, and (3) some multivariate methods (particularly PLS and PCR) can accommodate nonlinear spectral responses. Examination of FIG. 11, the graph of Correlation (between $O_2$ saturation and frequency) vs. Frequency, reveals that the correlation is in excess of 0.80 from 600 nm to 710 nm. In contrast, for frequencies above 850 nm, the correlation is less than 0.10. For purposes of comparison, FIG. 11 also shows the frequency regions used by New et al., Shaw et al. and the multivariate algorithms. Please note that: (1) the frequency regions used by Hoeft are not shown on the figure; and (2) the height of the various shaded regions is arbitrary. Also note that the widths illustrated for New et al. and Shaw et al. are wider than actually disclosed in these two references.

Figure 11:
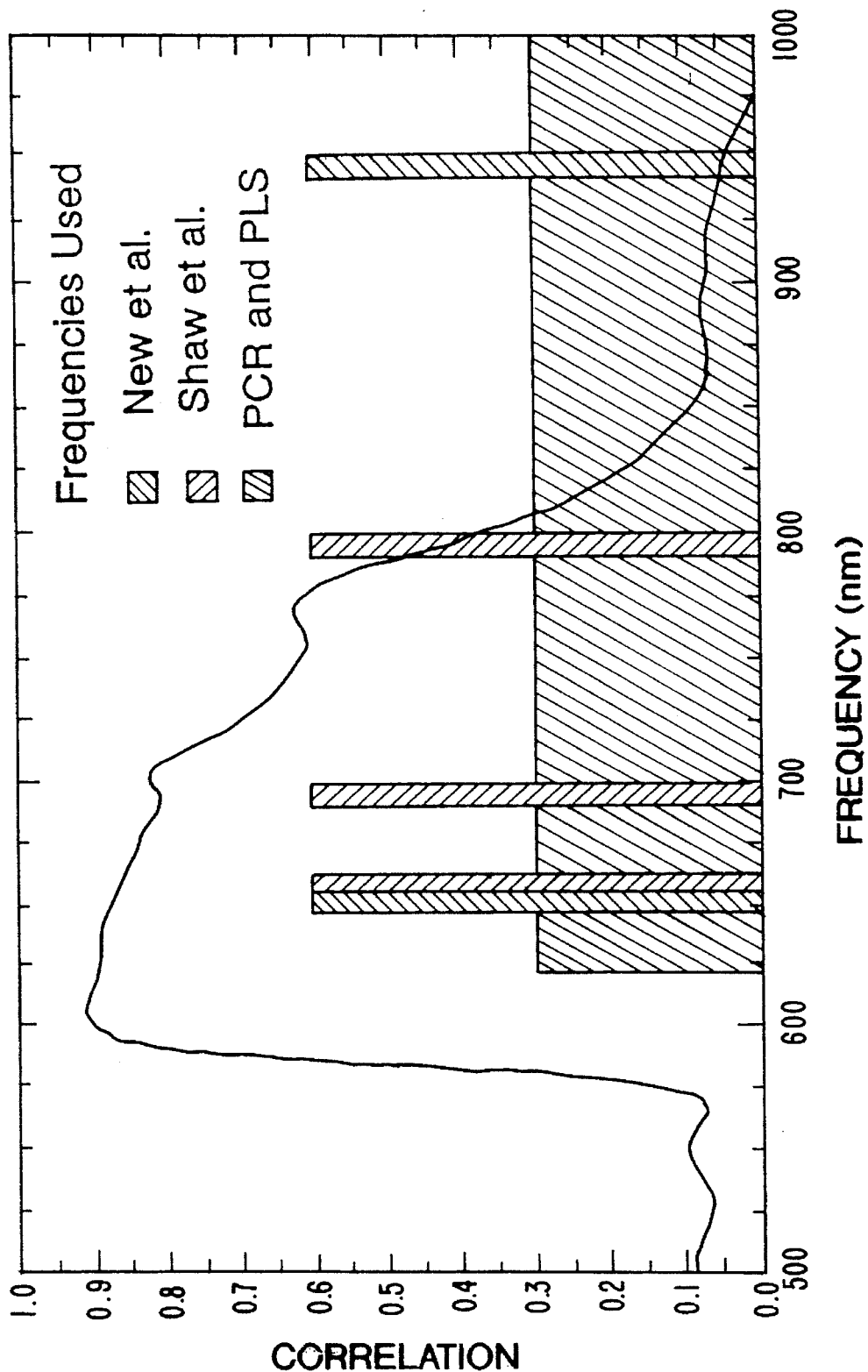
FIG. 11 is a graph illustrating the correlation between $O_2$ saturation and frequency and comparing the frequencies utilized by New, et al., Shaw, et al., and the multivariate algorithms of the present invention.

As illustrated in FIG. 11, our inclusion of all intensities in the spectral region (in contrast to the discreet limited regions utilized by the prior art) is beneficial to the analysis because most of these intensities contain considerable amounts of information relating to oxygen saturation. Consider the situation in which only one intensity at a given frequency or only several intensities at several discrete frequencies are used for the quantitative analysis. If one of the intensities at a selected frequency is significantly noisy or a spurious data value is recorded then the resulting oxygen saturation determination may be significantly inaccurate. In contrast, in a multivariate full-spectrum method, intensities at all frequencies are utilized and a significant signal averaging effect is observed. The multivariate full-spectrum signal averaging effect arises from the fact that information about each analyte or property is contained at many wavelengths and the statistical analysis serves to simultaneously use all this information. In addition a spurious data point at a given wavelength will be only one of many data points included in the analysis and its influence in the analysis will be diminished. Thus, the relative weight of the intensity of a particular frequency is decreased, and its adverse effect on the quantitative analysis is minimized.

An additional advantage of multivariate methods is their ability to model nonlinear relationships between the spectra and concentration. Our experience in determining blood oxygen saturation using reflected light has demonstrated that the relationship between reflected light intensity and oxygen saturation is nonlinear. The sources of this nonlinearity are at least partially due to instrument/detector nonlinearities and the sigmoidal oxygen-hemoglobin binding curve.

Hemoglobin is an allosteric protein, since the binding is cooperative. That is, the binding of oxygen at one heme facilitates the binding of the oxygen to other hemes. See Biochemistry, Lubert Stryer, 1975, W. H. Freeman and Company, pages 65–82. This cooperative binding effect results in a sigmoidal oxygen dissociation curve, as illustrated in FIG. 41-8 of the Textbook of Medical Physiology, 7th edition, Arthur C. Guyton, 1986, W. B. Saunders Company, page 496. Examination of the dissociation curve demonstrates that the relationship between the partial pressure of oxygen and the saturation is essentially linear above about 75% to 80% $O_2$ saturation. Below 75% the curve becomes sigmoidal and is no longer linear. As was previously described, analysis of our data also demonstrates that the relationship between the intensity of the reflected light and oxygen saturation also becomes nonlinear at approximately 75%.

Figure 12:
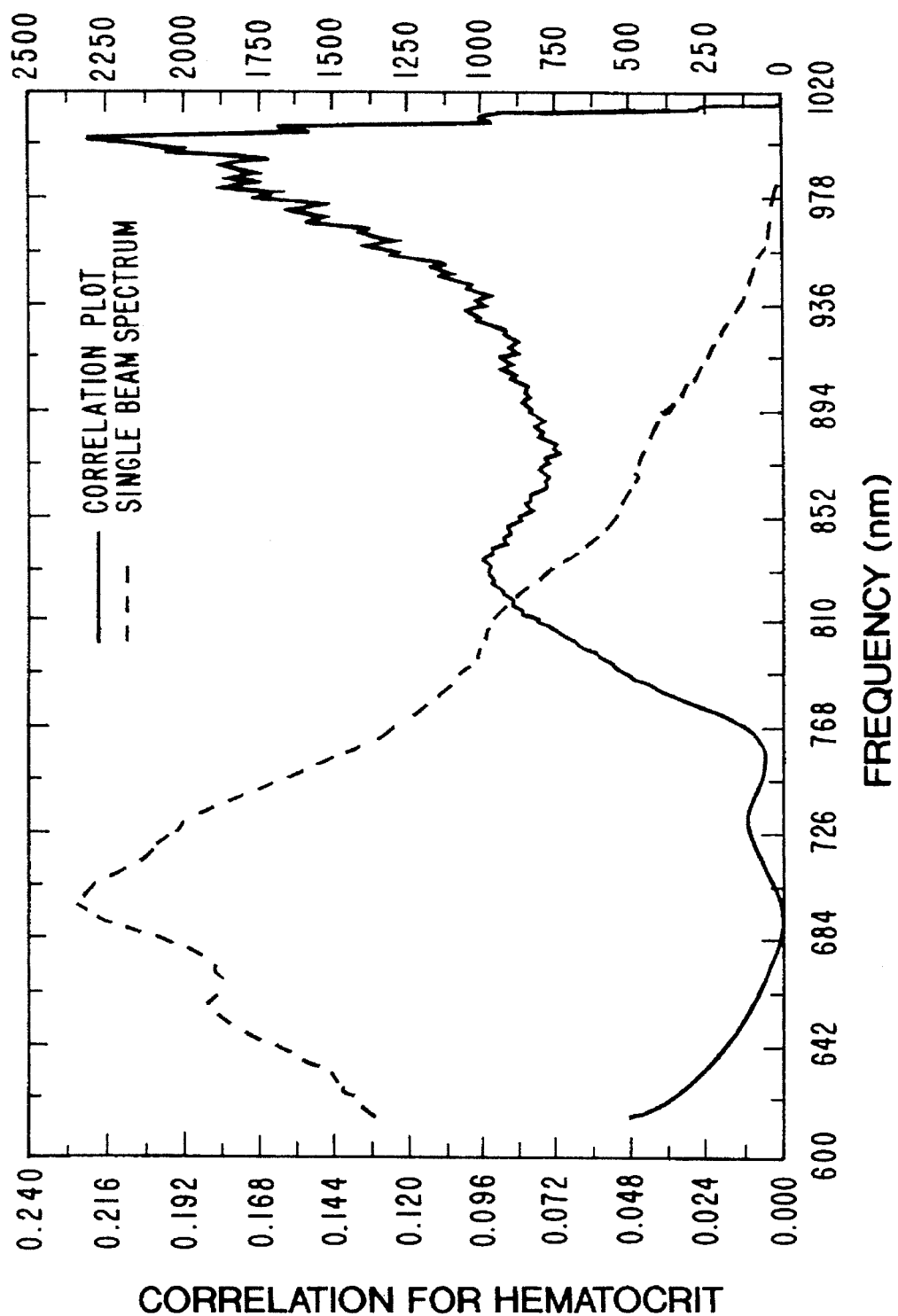
FIG. 12 is a graph illustrating the correlation between hematocrit and frequency, concurrently illustrated is a typical single beam spectra obtained from the blood samples.
Figure 13:
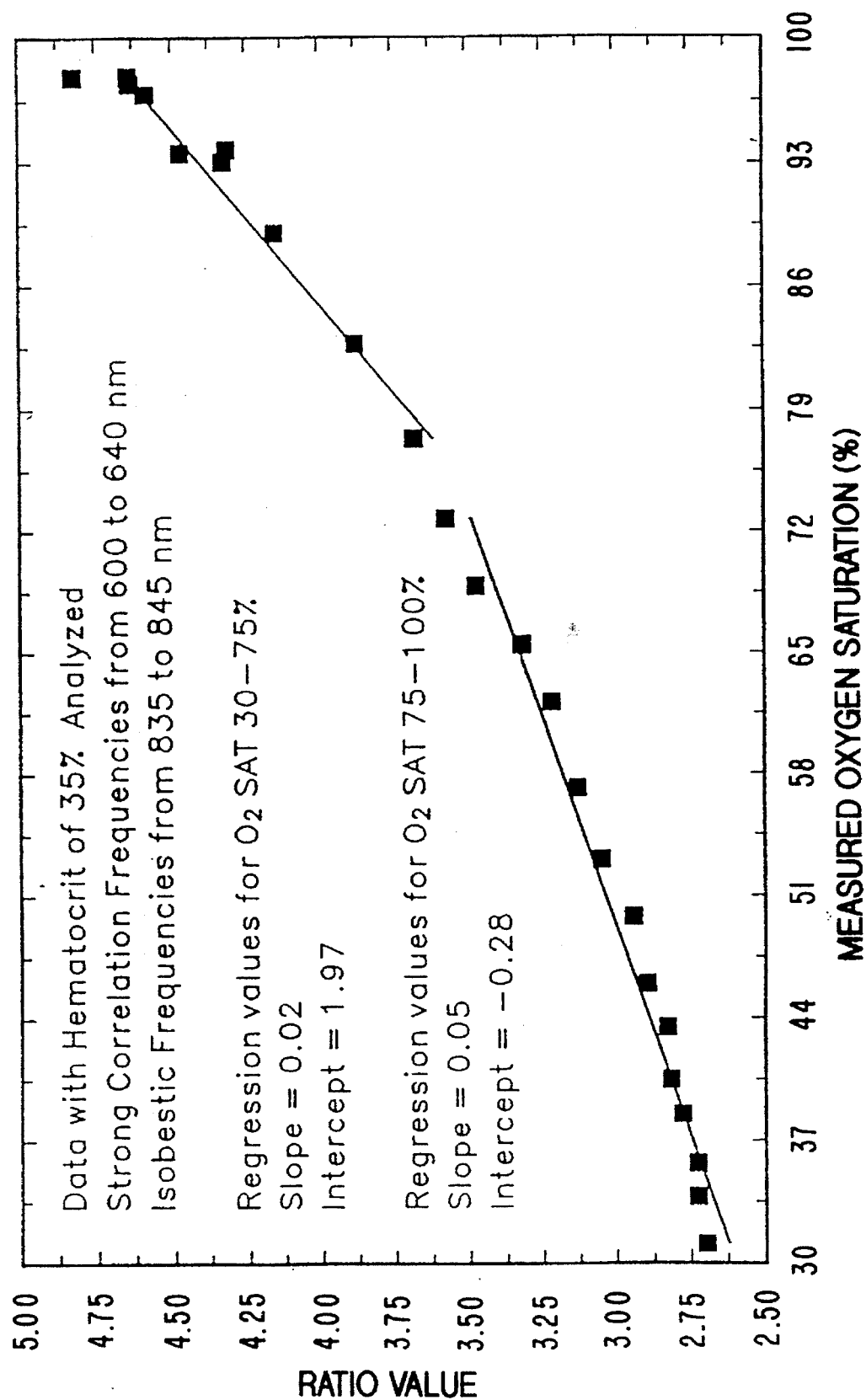
FIG. 13 is a graph illustrating the nonlinear relationship between a ratio of reflected light intensities and oxygen saturation; wherein the ratio is that of intensity values from an area of strong oxygen saturation correlation divided by intensity values from a region with isobestic characteristics, two independent regressions shown.

In the case of New et al., the algorithm for saturation determination uses a ratio of two specific frequencies which have a nonlinear response. To demonstrate that the nonlinear relationship between reflected intensity and oxygen saturation is not a phenomenon associated with only a few frequencies (or specifically the New, et al. ratio) a new ratio using intensities from a broad spectral region was calculated. With reference to FIG. 11, the numerator of the ratio was calculated from the intensity values at frequencies showing a strong correlation with oxygen saturation, specifically 600 nm to 640 nm. With reference to FIG. 12, the denominator of the ratio was calculated from wavelengths which have a strong isobestic correlation, specifically 835 nm to 845 nm. As previously described an isobestic wavelength contains information on red blood cell concentration, but does not change intensity with oxygen saturation. Thus, use of intensity values from an area with a strong isobestic correlation will provide the best possible reference for ratioing, as the effects of hematocrit variation and base line variation receive compensation. Intensity values for frequencies with wavelengths greater than 845 nm were not included because, the magnitude of the signal from our instrument becomes quite small and noisier. With reference to FIG. 13, the plot of oxygen Saturation versus the calculated Ratio Values for the spectral regions described above at a hematocrit of 35% demonstrates the nonlinear response of the data. Separate least squares regression for values corresponding to saturations of greater than 75% and less than 75% demonstrate significant differences in the slope and intercept values for the two regressions. Thus, regardless of the frequencies used the relationship between reflected intensity and oxygen saturation or level is nonlinear over the required clinically useful range, which includes saturations below 75%.

In summary, the physiological and physical difficulties associated with fetal monitoring such as low pulse pressure and the necessity for reflectance sampling, which result in decreased signal-to-noise ratios and the nonlinear relationship between saturation and reflected light intensity, have led us to the conclusion that the utilization of full spectrum multivariate analysis, as set forth herein, is the correct approach. Analysis of the experimental data with multivariate methods and comparison with prior art algorithms demonstrates the superiority of our methodology and the associated instrumentation.

Principal component regression (PCR) and partial least squares (PLS) are similar methods of multivariate analysis. Both are factor analysis methods which are full spectrum in nature; both can model some nonlinearities; and both allow for detection of outliers. PLS and PCR are both factor-based methods which are capable of being full-spectrum methods. These methods have been explained and contrasted recently by Haaland et al. "Comparison of Multivariate Calibration Methods for Quantitative Spectral Analysis:, *Analytical Chemistry,* 1990 Vol 62, No 10, May 5, pp 1090–1099. PLS and PCR can be employed even when the concentrations or properties of only one component are known in the calibration samples. Both PLS and PCR methods factor the spectral data calibration matrix into the product of two smaller matrices. This amounts to a data compression step where the intensities at all frequencies used in the analysis are compressed to a small number of intensities in a new full spectrum coordinate system. This new coordinate system is composed of loading vectors that can be used to represent the original spectral data. The intensities in the new full-spectrum coordinate system (called scores) are then used in a model where concentration is presumed to be a linear function of these intensities. Thus, PLS and PLS are methods that are concerned with modeling both spectra and concentrations during calibration. PCR performs the factoring of the spectral data matrix without using information about concentration. Therefore, there is no guarantee that the full-spectrum basis vectors that are associated with PCR are relevant for concentration prediction. PLS, on the other hand, performs the spectral factoring by trying to account for the spectral variation while assuming that the new basis vectors correlate with the calibration concentrations. Thus, PLS sacrifices some fit of the spectral data relative to PCR in order to achieve better correlations to concentrations during prediction.

Principle Component Regression

Figure 14:
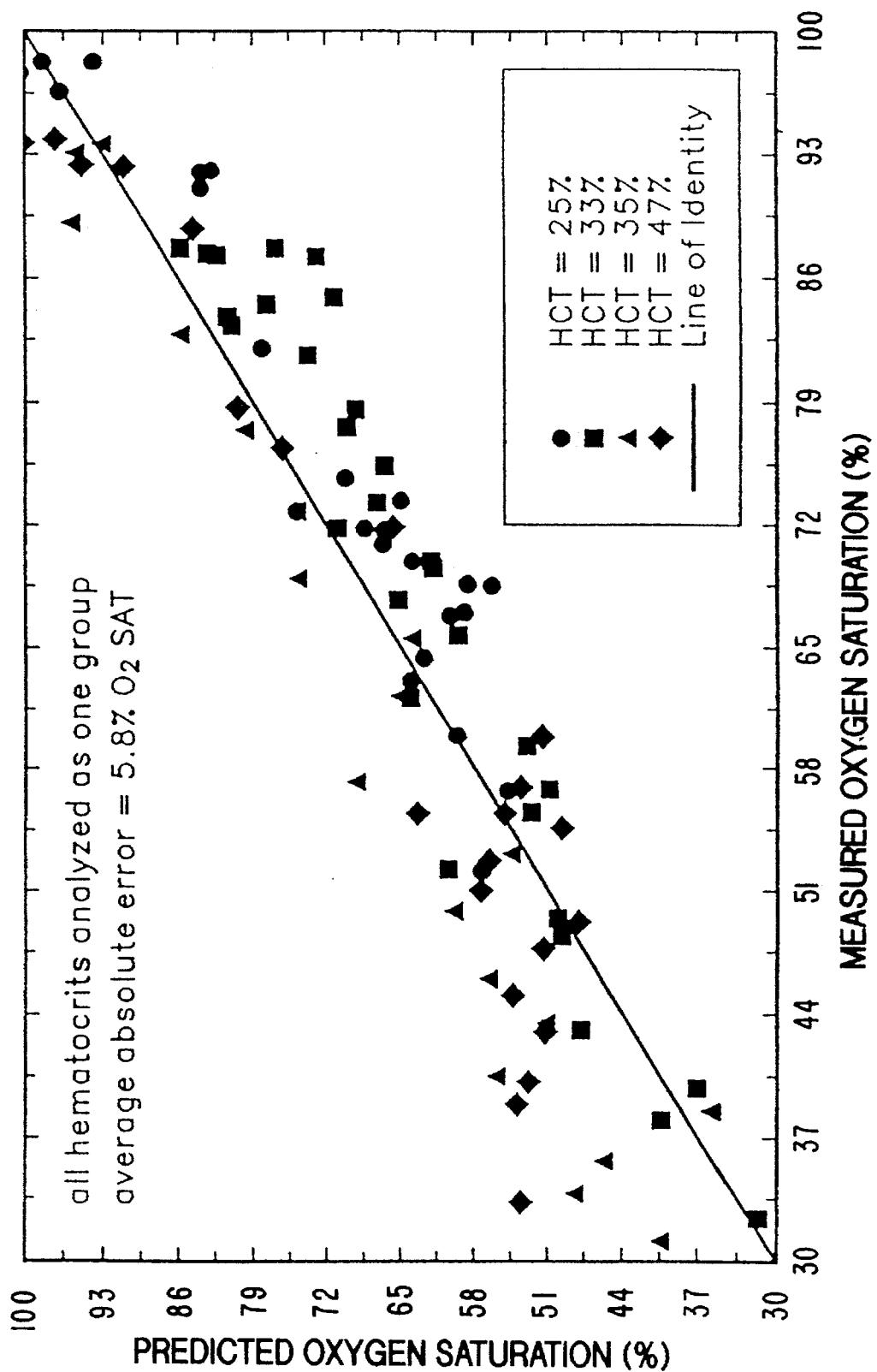
FIG. 14 is a plot of measured oxygen saturation vs. oxygen saturation predicted by analysis of the single beam spectra with the principle component regression (PCR) algorithm.

Analysis of the single-beam spectral data by PCR was performed for each hematocrit individually and then upon the entire data set (i.e., all hematocrits together). The results of the analysis are as illustrated in FIG. 14. The average errors are set forth in Table 4.

TABLE 4

| Hematocrit | Average Absolute Error of Percent Oxygen Saturation |
| --- | --- |
| 25% | 1.8 |
| 33% | 1.2 |
| 35% | 1.2 |
| 47% | 0.4 |
| all together | 2.3 |

Partical Least Squares

Figure 15:
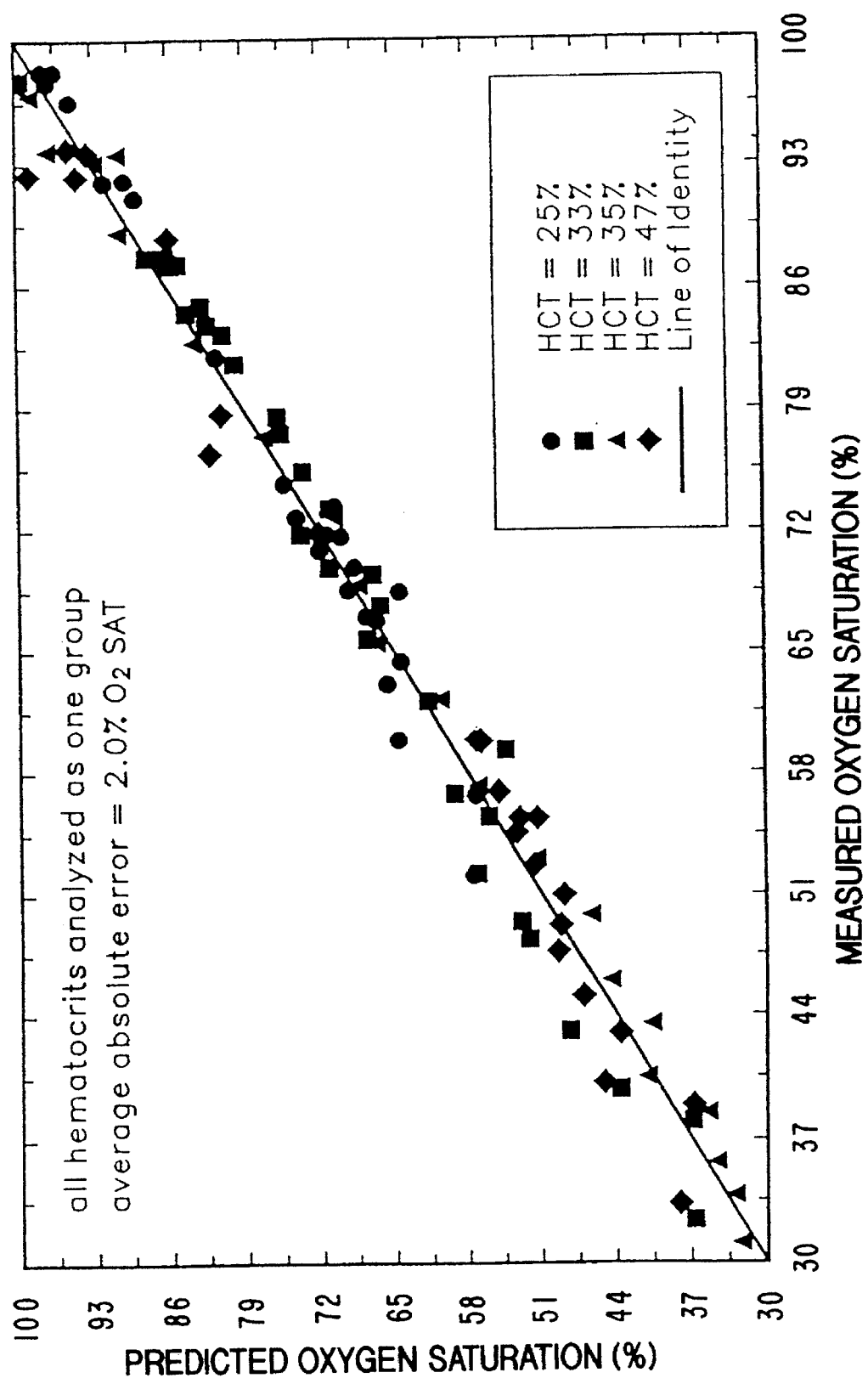
FIG. 15 is a plot of measured oxygen saturation vs. oxygen saturation predicted by analysis of single beam spectra with the partial least squares (PLS) algorithm.

The analysis of the single beam spectral data by PLS was, like PCR, preformed for each hematocrit individually and then upon the entire data set (i.e., all hematocrits together). The results of the analysis are illustrated in FIG. 15. The average errors are set forth in Table 5.

TABLE 5

| Hematocrit | Average Absolute Error of Percent Oxygen Saturation |
|---|---|
| 25% | 0.6 |
| 33% | 1.2 |
| 35% | 1.0 |
| 47% | 1.6 |
| all together | 2.0 |

Analysis with the Addition of Noise

As has been discussed previously, the fetal environment represents a condition in which the "additional" blood spectrum will have poor signal-to-noise ratio characteristics. The experimental spectral data used for the comparison analysis set forth above, was acquired in a manner to minimize noise. Specifically, the blood sample was scanned 128 times and the reflectance intensity values at a given wavelength were subsequently averaged to minimize random noise.

Figure 16:
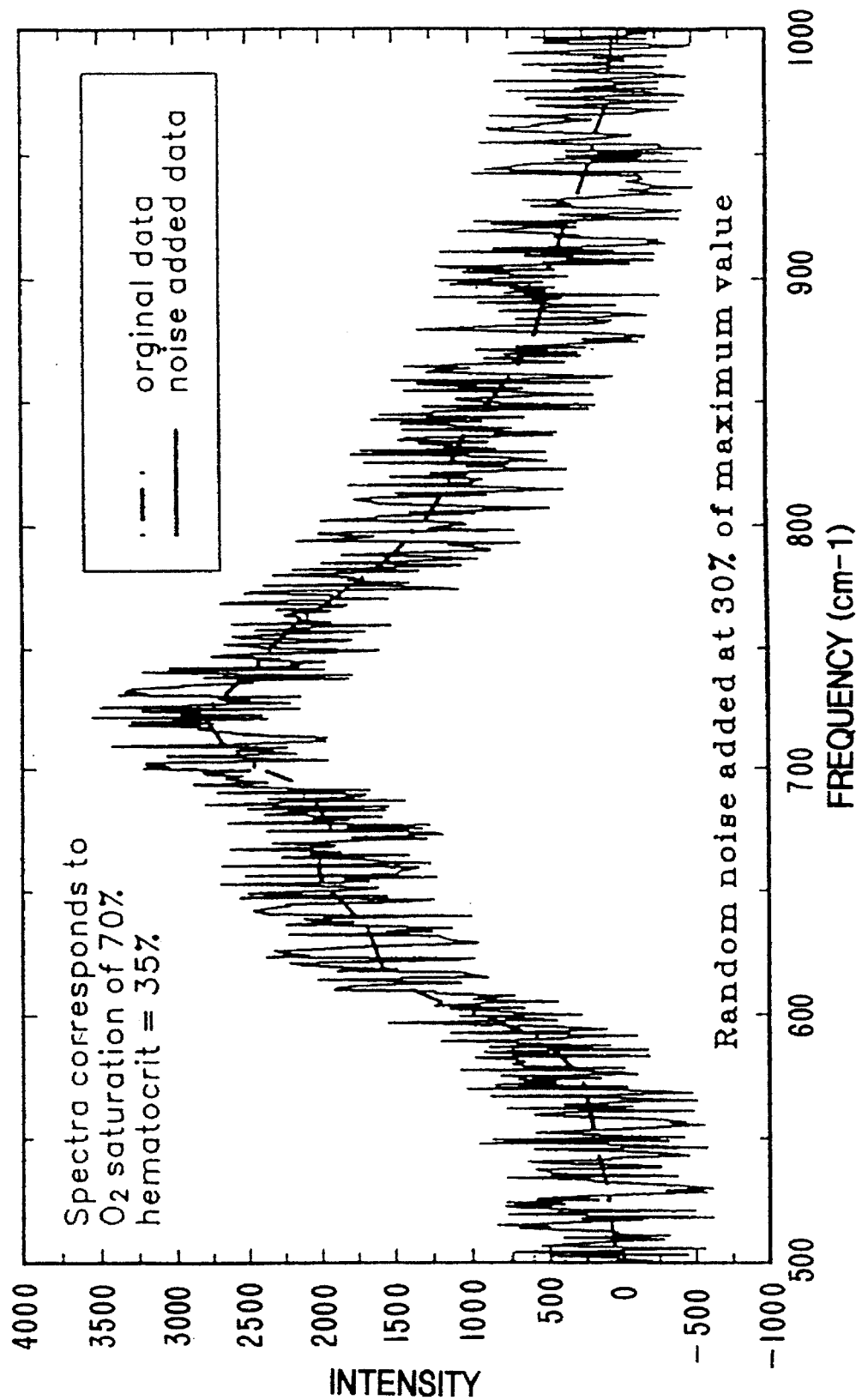
FIG. 16 is a graph illustrating the addition of random noise to a single-beam spectrum corresponding to a sample with $O_2$ saturation of 70% and a hematocrit (HCT) of 35%.

To simulate the noise level anticipated when monitoring an actual fetus, random computer generated noise was added to the original data. A charge coupled device (CCD) detector is a silica based detector and can be modeled as having noise characteristics independent of the magnitude of the signal and independent of the wavelength measured. Thus, the anticipated fetal spectral noise was added at a level of 30% of the average maximum value of all the spectra, and the intensity values at all wavelengths were subjected to the same magnitude and distribution of random noise. FIG. 16 sets forth a visual presentation on the amount of noise added. The specific spectrum shown corresponds to an $O_2$ saturation of 70% and a hematocrit of 35%. The resulting noisy spectral data, from all data points, were then analyzed using the same algorithms as described above. The analysis of the noisy data were done in exactly the same way as the original data. The results of the analysis, which are shown below, clearly demonstrate the superiority of multivariate analysis.

Figure 17:
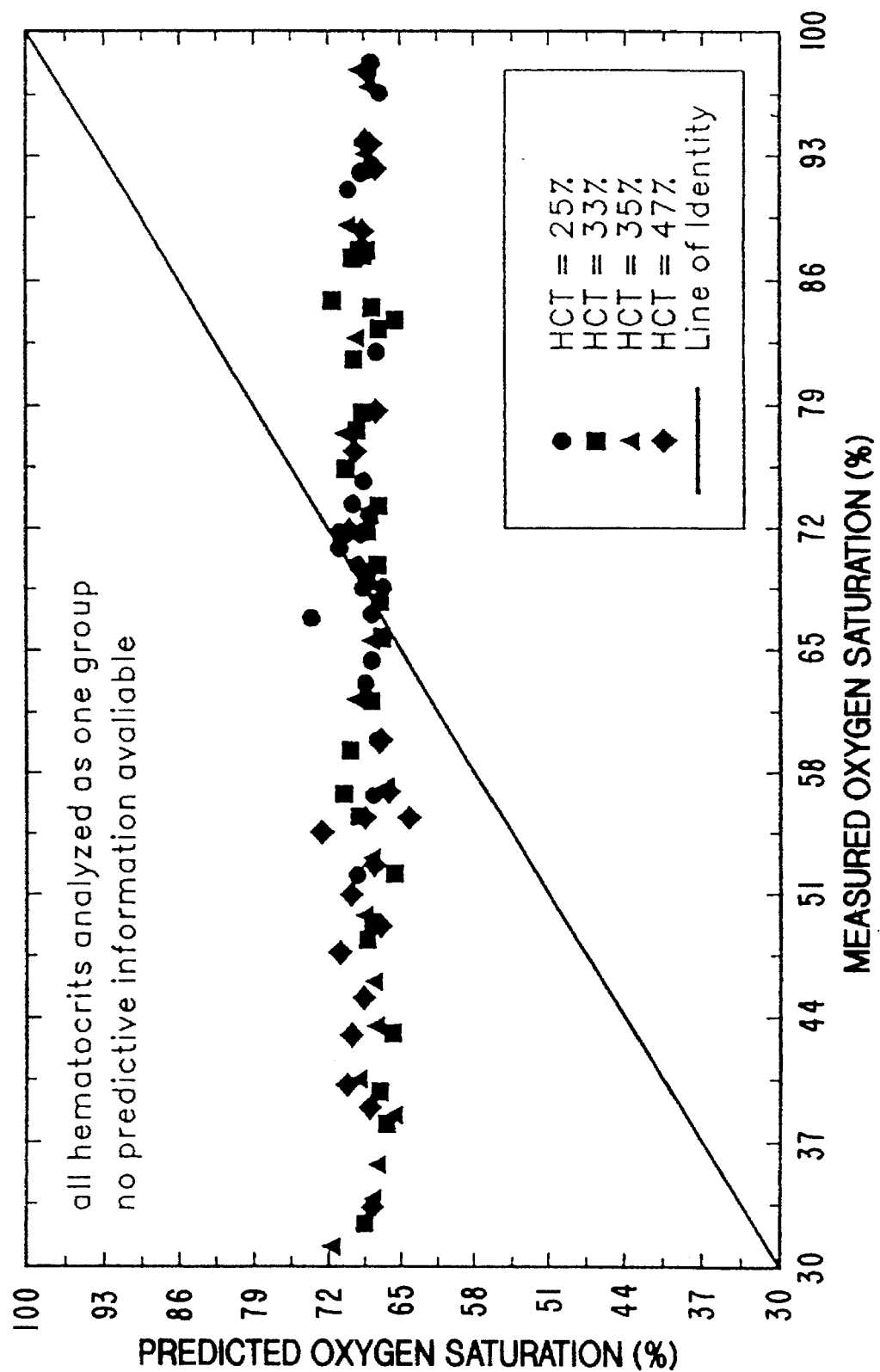
FIG. 17 is a plot of measured oxygen saturation vs. oxygen saturation predicted by the analysis of single-beam spectra (with noise added) with the algorithm of New, et al.

The New et al. algorithm was applied to the noisy spectra in the manner as previously described. As can be seen from FIG. 17, the results of the analysis did not have any predictive value. The actual results are summarized below:

TABLE 6

| Hematocrit | Average Absolute Error of Percent Oxygen Saturation |
|---|---|
| 25% | 16.5 |
| 33% | 13.2 |
| 35% | 11.3 |
| 47% | 19.7 |
| all together | 16.0 |

Figure 18:
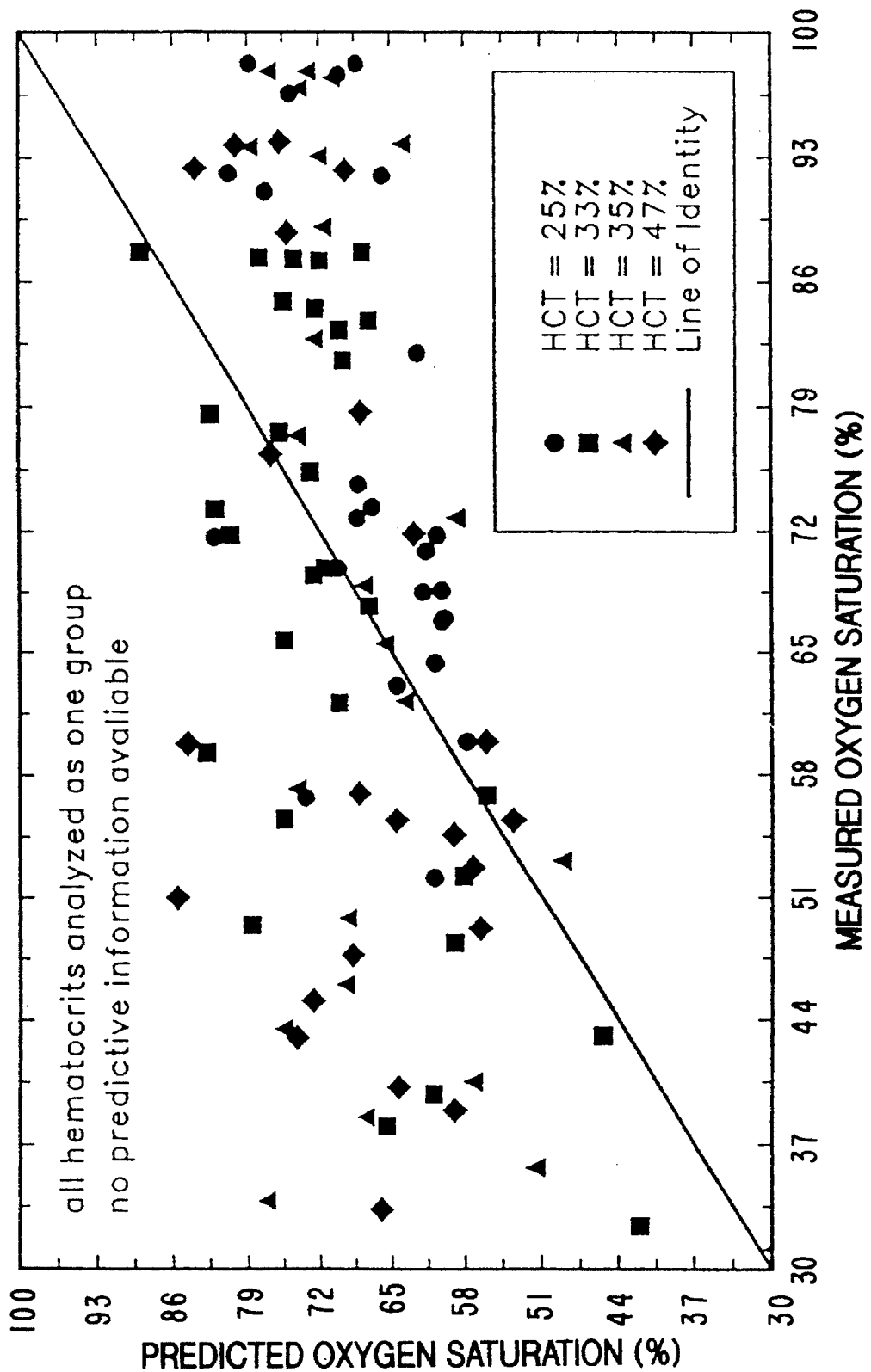
FIG. 18 is a plot of measured oxygen saturation vs. oxygen saturation predicted by the analysis of single-beam spectra (with noise added) with the algorithm of Hoeft, et al.

The Hoeft et al. algorithm was applied to the noisy spectra in the same manner as previously described. Again, the results of the analysis did not have any predictive value. See FIG. 18. The actual results are summarized below:

TABLE 7

| Hematocrit | Average Absolute Error of Percent Oxygen Saturation |
|---|---|
| 25% | 16.0 |
| 33% | 11.0 |
| 35% | 9.2 |
| 47% | 18.1 |
| all together | 13.6 |

Figure 19:
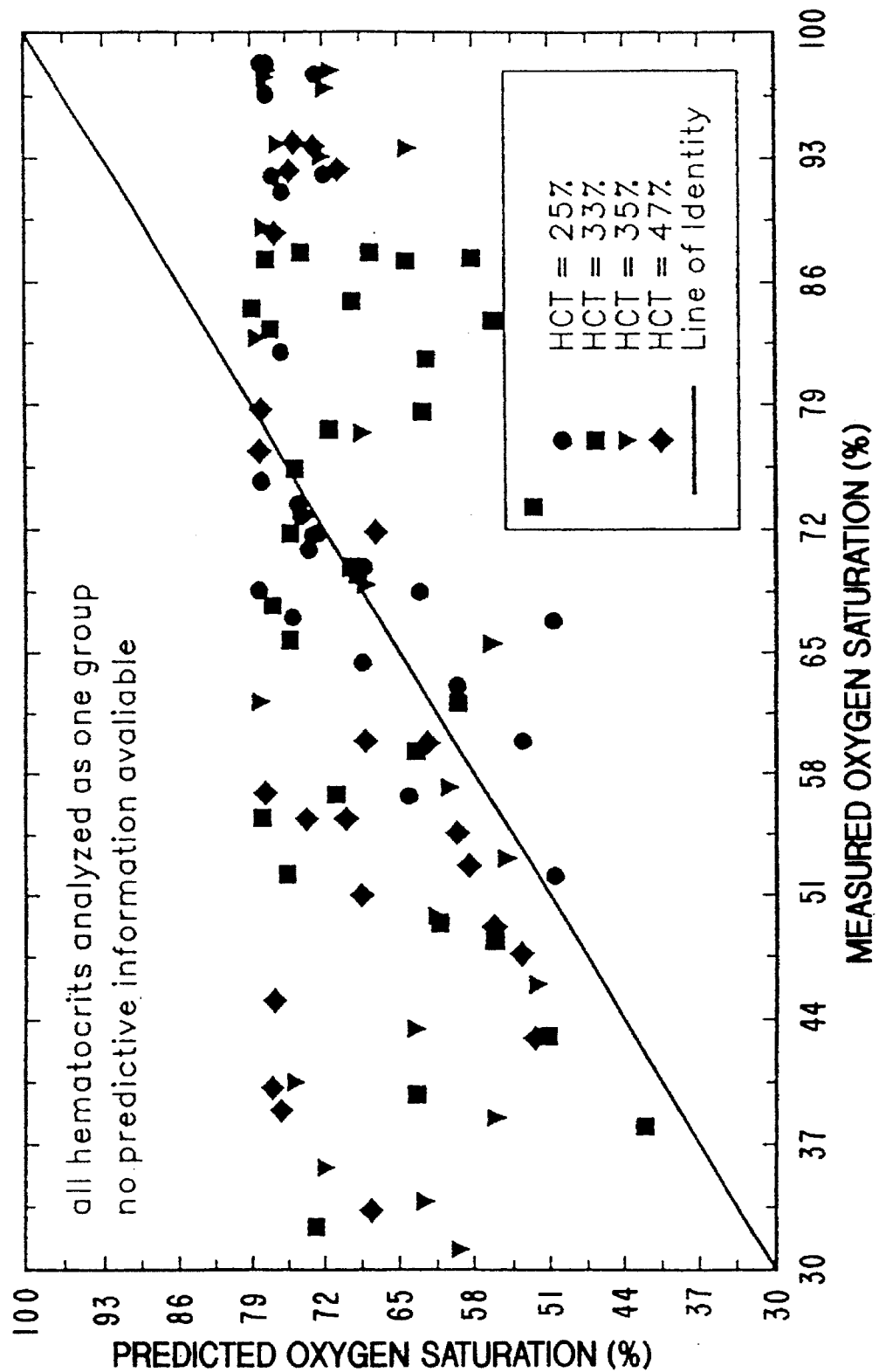
FIG. 19 is a plot of measured oxygen saturation vs. oxygen saturation predicted by the analysis of single-beam spectra (with noise added) with the algorithm of Shaw, et al.

The Shaw et al. algorithm was also applied to the noisy spectra in the manner as previously described with regard to non-noisy data. As with New et al. and Hoeft et al., and as illustrated in FIG. 19, the results of the analysis did not have any predictive value. The actual results are summarized in Table 8.

TABLE 8

| Hematocrit | Average Absolute Error of Percent Oxygen Saturation |
|---|---|
| 25% | 15.5 |
| 33% | 12.7 |
| 35% | 8.0 |
| 47% | 14.5 |
| all together | 13.6 |

Figure 20:
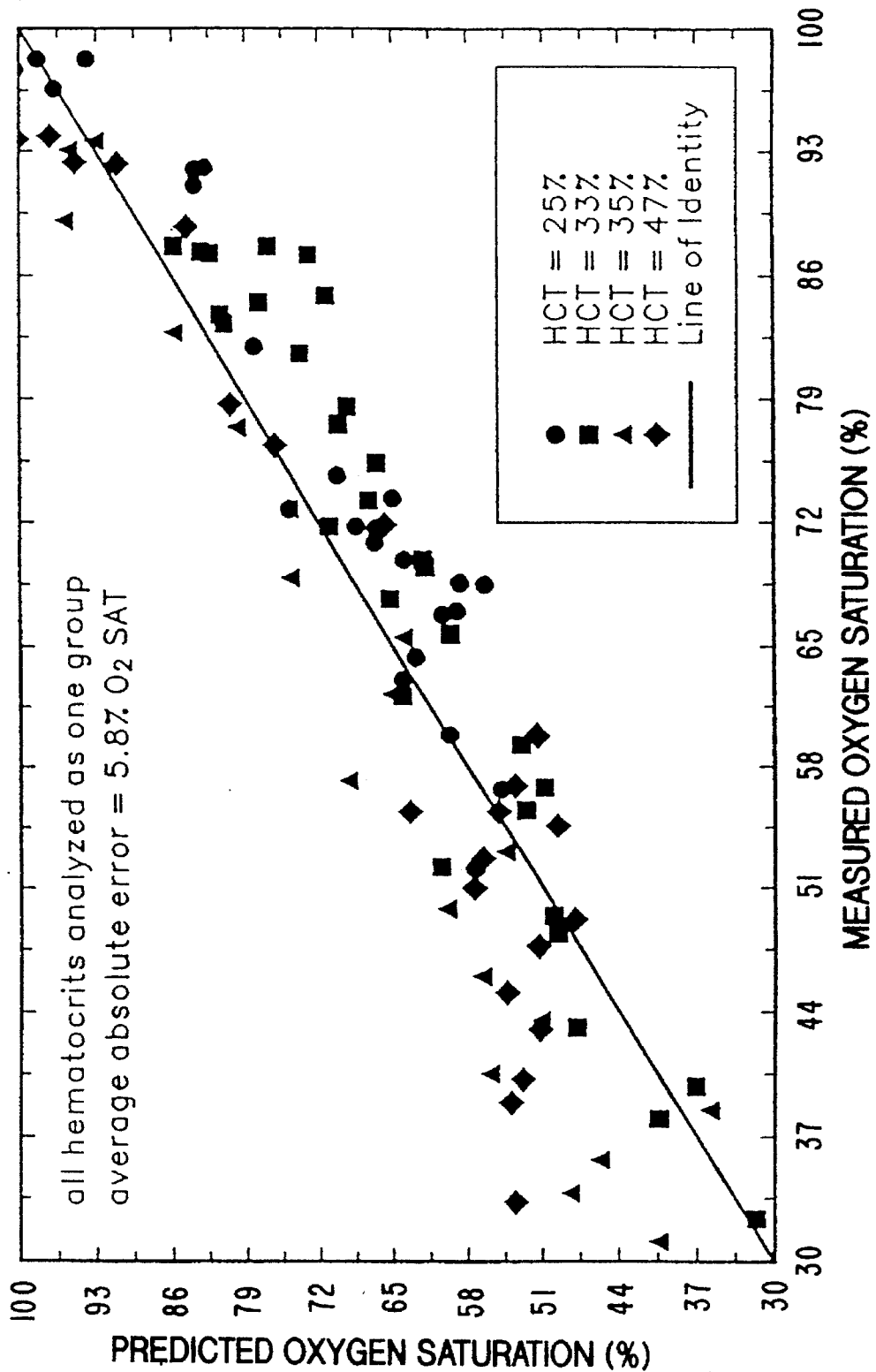
FIG. 20 is a plot of measured oxygen saturation vs. oxygen saturation predicted by the analysis of single-beam spectra (with noise added) with the PCR algorithm.

The principle component regression algorithm was applied to the noisy spectra in the manner as previously described. In contrast to New et al., Hoeft et al. and Shaw et al., the results of the analysis, illustrated in FIG. 20, showed only a mild decrease in predictive ability. Thus the PCR algorithm still performed well. The actual results are summarized below:

TABLE 9

| Hematocrit | Average Absolute Error of Percent Oxygen Saturation |
|---|---|
| 25% | 3.7 |
| 33% | 3.4 |
| 35% | 3.8 |
| 47% | 4.2 |
| all together | 5.8 |

Figure 21:
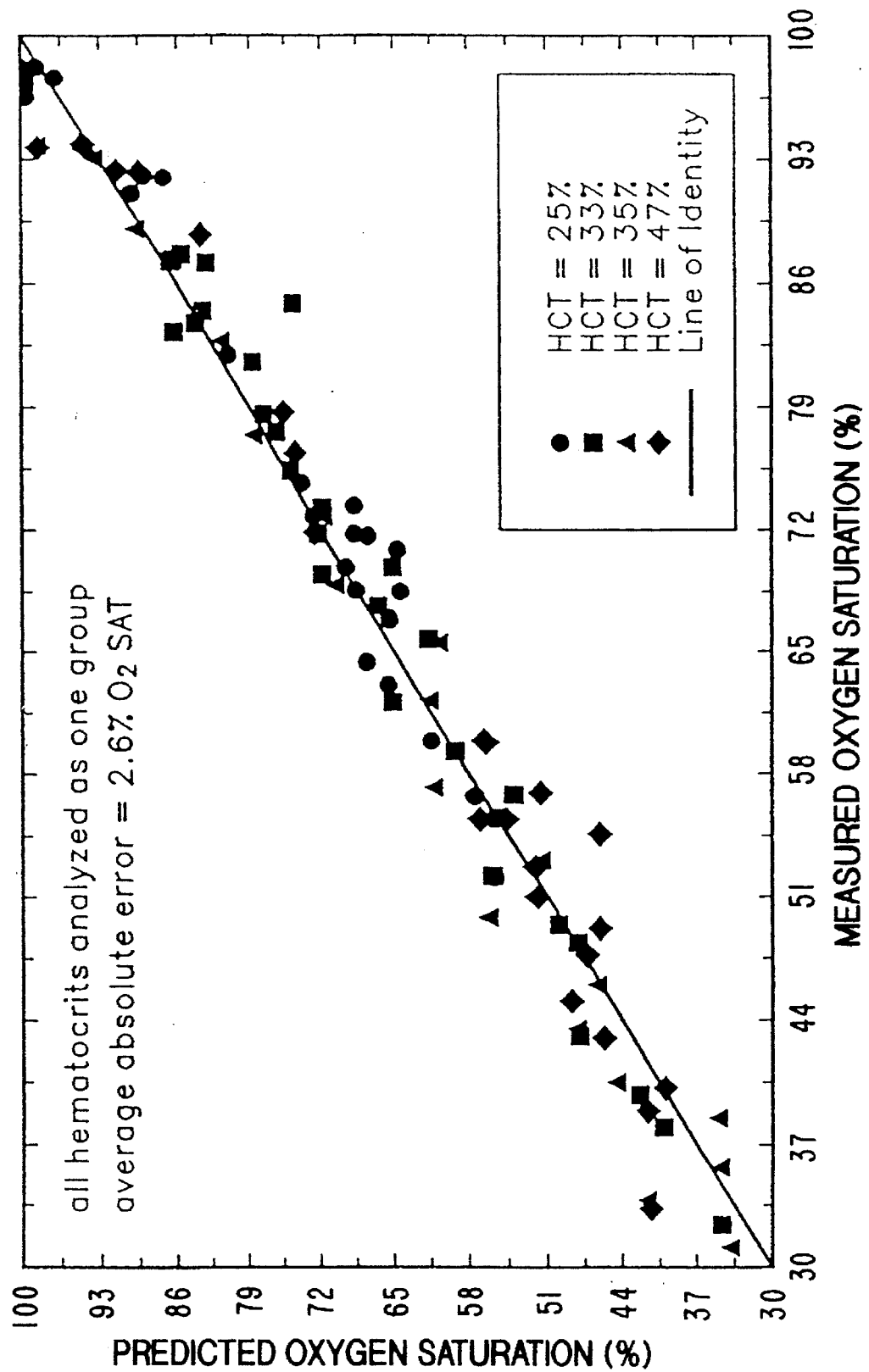
FIG. 21 is a plot of measured oxygen saturation vs. oxygen saturation predicted by the analysis of single-beam spectra (with noise added) with the PLS algorithm.

Finally, the partial least squares algorithm was applied to the noisy spectra in the manner as previously described. The results of the analysis showed a mild decrease in predictive value but the algorithm still preformed well, especially given the level of noise added to the spectral data. See FIG. 21. The average absolute error of prediction changed from 2.0 percent $O_2$ saturation using the non-noisy spectra to 2.6 percent $O_2$ saturation on the noisy spectra. The actual results are summarized below:

TABLE 10

| Hematocrit | Average Absolute Error of Percent Oxygen Saturation |
|---|---|
| 25% | 3.1 |
| 33% | 2.9 |
| 35% | 3.4 |
| 47% | 3.5 |
| all together | 2.6 |

Considering all hematocrit groups together results in a greater number of calibration samples which improves the precision of the analysis. This grouping results in a lower error for the "all together" set than any individual set. The ability to create a model which more completely models both linear and nonlinear variations with increasing calibration sample size is an important property of multivariate algorithms. In this case the PLS algorithm is able to more fully compensate for the nonlinearities in the oxygen saturation/level versus reflected intensities relationship. This improvement in modeling produces an increase in determination precision and is a characteristic of multivariate algorithms, and is not demonstrated by the New, et al., Shaw, et al., or Hoeft methods.

PLS with Isobestic Correction and Without Noise Added

Figure 22:
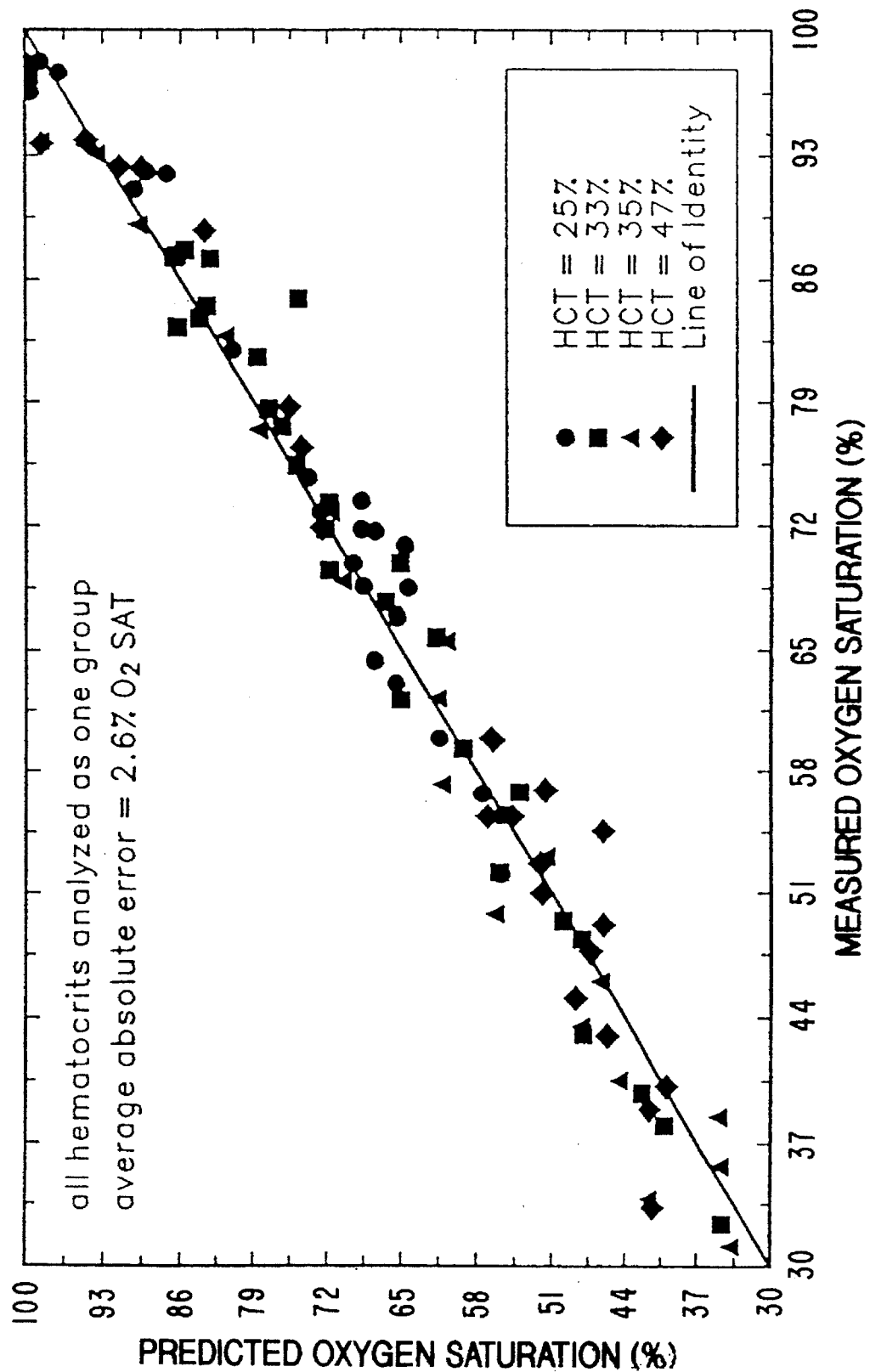
FIG. 22 is a plot of measured oxygen saturation vs. oxygen saturation predicted by analysis of isobestically ratioed single beam spectra with PLS with isobestic ratioing.

The original spectral data obtained contains information on oxygen saturation, hematocrit and other properties. If the data could be manipulated such that the effect of the hematocrit could be removed, then the analysis of the data for determination of oxygen saturation would be improved. As the data were obtained by reflection sampling an understanding of the scattering process is important. As was pointed out by the work of Zdrojkowski et al. "Optical Transmission and Reflection by Blood", *IEEE BME*, pp 122–128, light scattering within blood is mainly due to the back scattering at cell surfaces. Since almost all cells within the blood are erythrocytes (i.e., red blood cells), the mean scattering coefficient should depend directly on the hematocrit. In the experiment described herein the only cells present in solution were red blood cells because the starting blood solution was packed red blood cells. As has been previously described there exists isobestic wavelengths which contain information on blood concentration, but do not change intensity with oxygen saturation. Thus, ratioing the entire spectral data by the corresponding isobestic value effectively compensates for the influence of hematocrit variation. The correlation between each frequency and the hematocrit was calculated for the frequency region used in the multivariate analysis, FIG. 12. The correlation is quite poor and reaches a maximum value of 0.20. Although the correlation is higher at wavelengths greater than 940 nm, the intensity of the signal from our instrument deteriorates significantly. Despite the poor correlation, the single-beam spectra were ratioed using the isobestic frequency suggested by New et al. at approximately 940 nm. The isobestically ratioed data were then analyzed for each hematocrit individually, and as a single group. The results, as illustrated in FIG. 22, were significantly improved as evidenced in Table 11.

TABLE 11

| Hematocrit | Average Absolute Error of Percent Oxygen Saturation |
|---|---|
| 25% | 1.3 |
| 33% | 2.2 |
| 35% | 1.9 |
| 47% | 0.8 |
| all together | 1.5 |

It needs to be recognized that the foregoing isobestic ratioing procedure requires that the intensities at the frequencies used for determination of the isobestic value should have high signal-to-noise ratio characteristics. The reason for this requirement is that a spurious set of intensities in the isobestic region will cause the entire spectrum to be divided by a noisy and unreasonable number. Thus, the magnitude of the spectra will vary in a random fashion and predictive determination of oxygen saturation becomes difficult. The process of isobestic ratioing is advantageous in conditions where the data is not excessively noisy. Less noisy conditions exist if the spectral data were obtained on an adult in the normal non-invasive transmission sampling mode or with an invasive oximeter. Therefore, isobestic ratioing may not be useful in the principle application to fetal oximetry, but the ratioing technique would improve the results of the analysis if applied in a condition of less noise.

The Preferred Embodiment

With reference to FIG. 1, oximeter 111 includes a spectrometer 113, an electronics and computer processing module 115, and a visual display module 117. Spectrometer 113 includes a broad band halogen light source 121, a concave focusing mirror 123 a fiber optic housing 125, a second fiber optic housing 127, a grating 129, a CCD array detector 131, and an electric buss 135. Module 115 includes a microprocessor 141, memory 143 in which the multivariate calibration model is stored, and module 145 in which the outlier defection algorithm is stored. Microprocessor 141, memory 143 and module 145 are connected together via suitable electronic connectors, as illustrated schematically at 147. Visual display module 117 includes a blood oxygen saturation display 151, heart rate display 153, an indicator of accuracy of determination 155, oxygen saturation trend 157, and heart rate tracing 159. Finally, apparatus 111 includes a fiber optic bundle 161, including a central control input fiber 163, and a surrounding bundle of output fibers 165. In cross section bundle 161 has the configuration illustrated in FIG. 5A. The end of bundle 161 is secured to the scalp of the fetus via a suitable suction or other device.

Source 121 emits frequencies from approximately 500 mm to 1000 mm, as illustrated in FIG. 11. This light is transmitted to the fetus via input fiber 163 to illuminate a blood containing part of the fetus, such as the scalp illustrated in FIG. 1. The back scattered or reflected light is then transmitted back to spectrometer 113 by fiber bundle 165. Alternately the same optical fiber or a secondary optical fiber could be utilized. The returning light is then separated into various frequencies and detected by the charge coupled device (CCD) array detector 131.

The reflected light intensities at the various frequencies are then analyzed by computer 141 employing a multivariate algorithm (such as PLS or PCR) utilizing information over the entire spectral range. The spectral data are analyzed to establish which spectra correspond with maximum concentration of blood (or maximum dilation) in the arterial system of the fetus, and which spectra correspond with minimum concentration or dilation of the arterial system. The spectra associated with minimum dilation will contain information on blood, skin, bone, etc. The spectra associated with maximum dilation will contain the same information plus an additional amount of blood information. However, because reflected light does not necessarily follow a Beer's law model, data treatments or spectral transformations for reflection spectra may be different than for absorption spectra. Normally, diffusely reflected light is expected to follow the Kubelka-Munk relation, See J. R. Ferraro and A. J. Rein: "Application of Diffuse Reflectance Spectroscopy in the Far-Infrared Region," in Fourier Transform Infrared Spectroscopy, Applications to Chemical Systems, Vol. 4, Edited by J. R. Ferraro and L. J. Basile, *Academic Press, Inc., New*

York, 1985, pp. 244–282, and M. P. Fuller and P. R. Griffiths, *Applied Spectroscopy*, 1980, Vol. 34, pp. 533–534. The Kubelka-Munk equation is as follows:

$$f(R_\infty)=(1-R_\infty)/2T_\infty=k/s$$

where $R_\infty$ is the absolute reflectance of an "infinitely thick" layer, s is the scattering coefficient, and k is the molar absorption coefficient. Since $f(R_\infty)$ is approximately proportional to sample concentration, spectra converted to Kubelka-Munk units are nearly equivalent to absorption spectra. In practice, $R_\infty$ can be estimated from the ratio of the sample and reference single-beam spectra. However, in spite of this theoretical justification for the Kubelka-Munk relation, the log of the inverse reflectance sometimes yields superior quantitative results. Subtraction of the appropriately transformed spectral data from the maximum and minimum dilation will correspond to the additional amount of blood present due to the pulse pressure generated by the heart. The above process effectively subtracts out the interfering background and provides the multivariate algorithm with a spectrum corresponding to the additional blood. The subtracted spectrum is analyzed by a multivariate algorithm. In the preferred embodiment the algorithm employed would be partial least squares or principle component regression. The algorithm will provide the operator with blood oxygen saturation as indicated by 151.

An additional embodiment of the invention includes apparatus for obtaining information regarding the electrical activity of the fetal heart, which activity can provide information to assist in determination of maximal and minimal dilation. With reference to FIG. 23, maximum expansion of the arterial system due to ventricular contraction occurs at a set interval following the R peak of the QRS complex. The QRS complex is created by the depolarization of the ventricular muscle. This complex precedes ventricular contraction which results in ejection of blood from the heart. The time between the R peak of the QRS complex and maximum expansion of the arterial system is approximately 0.08 seconds and varies only slightly with heart rate. Minimum expansion of the arterial system is present prior to ventricular contraction and corresponds to a time period in the vicinity of the P-wave. The P-wave results from depolarization of the atrial muscle. The time of minimum expansion is related to both the R peak of the QRS complex and heart rate. Correlation with the electrical activity of the heart may be necessary for effective operation during periods of maximum uterine contraction. If the fetus were in normal vertex position the head could become compressed to the point that the pulse pressure or change in diameter of the vascular system becomes too small to detect rapidly using optical methods. Thus, the electrical activity of the fetal heart would provide the additional information for operation under adverse conditions.

It is the authors' experience that pretreatment of the spectral or concentration data can oftentimes improve the analysis precision in the calibration and unknown analyses as well as increase the robustness of the models. Thus, data pretreatments including but not limited to centering, scaling, normalizing, taking first or higher order derivatives, smoothing, Fourier transforming, and/or linearization can all improve the analysis precision and accuracy. These pretreatments can also improve the robustness of the model to instrument drift and can improve the transfer of the calibration model between instruments.

It is additionally understood by the inventors that the amount of oxygen in the blood can be recorded as oxygen saturation or partial pressure of oxygen. These two indicators of oxygen level are strongly correlated, although partial pressure of oxygen will be affected by pH and the partial pressure of carbon dioxide. Determination of oxygen saturation is referenced in the specification due to its present use in clinical practice.

Whereas the drawings and accompanying description have shown and described the preferred embodiment of the present invention, it should be apparent to those skilled in the art that various changes may be made in the form of the invention without affecting the scope thereof.

We claim:

1. A quantitative analysis instrument for noninvasive measurement of blood oxygen saturation in a fetus, said instrument comprising:

a. a source of at least four different wavelengths of light, at least some of said wavelengths being in the range from 500 to 1000 nm;

b. optical means for introducing said wavelengths into said fetus and for collecting at least a portion of said wavelengths that are reflected back from said fetus;

c. a device for positioning said optical means relative to said fetus, whereby at least a portion of said wavelengths are introduced into said fetus and said portion of said reflected wavelengths are collected;

d. at least one detector positioned relative to said optical means for measuring the spectral intensities of said reflected wavelengths during the diastolic portion of the cardiac cycle of said fetus, to obtain a diastolic set of spectral intensities v. wavelengths, and for measuring the spectral intensities of said reflected wavelengths during the systolic portion of said cardiac cycle, to obtain a systolic set of spectral intensities v. wavelengths;

e. electronics including a microprocessor and memory means for, (i) storing said diastolic set of spectral intensifies v. wavelengths and said systolic set of spectral intensities v. wavelengths; (ii) processing said diastolic and systolic sets of spectral intensities to determine a measure of change between said diastolic and systolic sets to obtain a third set of spectral intensifies v. wavelengths, and (iii) processing said third set of spectral intensifies v. wavelengths to determine a measure of oxygen saturation, said memory means including a multivariate algorithm and a multivariate calibration model, said algorithm using at least three variables; and f. means, for indicating said determined measure of oxygen saturation.

2. The analysis instrument of claim 1, wherein said algorithm is selected from the group including PLS, PCR, CLS, Q-matrix, cross-correlation, Kalman filtering and MLR.

3. The analysis instrument of claim 2, wherein said algorithm is an algorithm capable of utilizing more discrete spectral intensities per sample than the number of calibration samples used to generate said model.

4. The analysis instrument of claim 1, wherein said electronics also includes an electrode for measuring the electrical activity of the heart of said fetus, to facilitate the determination of said systolic portion and said diastolic portion of said cardiac cycle.

5. The analysis instrument of claim 1, wherein said electronics further includes means for detecting outliers.

6. A method for noninvasive measurement of blood oxygen saturation in a fetus, said method comprising the steps of:

a. generating at least four different wavelengths of light, some of said wavelengths being in the range from 500 to 1000 nm;

b. irradiating said fetus with said wavelengths and collecting a portion of said wavelengths that are reflected back from said fetus;

c. measuring the spectral intensities of said reflected wavelengths during the diastolic portion of the cardiac cycle of said fetus, to obtain a diastolic set of spectral intensities v. wavelengths, and measuring the spectral intensities of said reflected wavelengths during the systolic portion of said cardiac cycle, to obtain a systolic set of spectral intensities v. wavelengths; and d. determining a third set of spectral intensities v. wavelengths from said diastolic and systolic sets of spectral intensities, and determining a measure of oxygen saturation from said third set of spectral intensities v. wavelengths utilizing a multivariate algorithm and a multivariate calibration model, said algorithm using at least three variables.

7. The method as set forth in claim 6, wherein said step of determining oxygen saturation includes utilizing an algorithm selected from the group including PLS, PCR, CLS, Q-matrix, cross-correlation, Kalman filtering and MLR.

8. The method as set forth in claim 7, wherein said algorithm is capable of utilizing more discrete spectral intensities per sample than the number of calibration samples used to generate said model.

9. The method as set forth in claim 6, further including the step of determining whether said third set of spectral intensities v. wavelengths from said fetus is an outlier by comparing said third set of spectral intensities v. wavelengths from said fetus with a set of spectral intensities v. wavelengths obtained from irradiating calibration samples.

10. The method as set forth in claim 9, wherein said determination of whether said third set of spectral intensities v. wavelengths from said fetus represents an outlier includes the step of comparing said third set of spectral intensities v. wavelengths from said fetus to said set of spectral intensities v. wavelengths from said calibration samples, to determine a measure of the magnitude of the difference between said third set of spectral intensities v. wavelengths from said fetus and said set of spectral intensities v. wavelengths from said calibration samples.

11. The method as set forth in claim 10, further including using a statistical test to indicate the probability of said magnitude being caused by random chance, and further including the step of classifying said third set of spectral intensities v. wavelengths from said fetus as representing an outlier when said probability is determined to be too low.

12. The method as set forth in claim 6, further including the step of pretreating of said sets of spectral intensities v. wavelengths from said fetus.

13. The method as set forth in claim 12, wherein said pretreating includes the steps of centering, scaling, normalizing, taking first or higher order derivatives, smoothing, fourier transforming or linearization.

14. The method as set forth in claim 6, including accomplishing said determination of said diastolic portion and said systolic portion of said cardiac cycle by concurrently measuring the electrical activity of the heart of said fetus.

\* \* \* \* \*